(12) United States Patent
Allam et al.

(10) Patent No.: US 12,329,171 B1
(45) Date of Patent: *Jun. 17, 2025

(54) NATURAL FOOD PRESERVATIVE

(71) Applicant: IMAM MOHAMMAD IBN SAUD ISLAMIC UNIVERSITY, Riyadh (SA)

(72) Inventors: Ahmed Aly Ahmed Allam, Riyadh (SA); Hassan Ahmed Rudayni, Riyadh (SA); Rehab Khaled Mahmoud, Beni-Suef (EG); Nabil Sayed Hafez, Faiyum (EG); Naif Ghazi Altoom, Riyadh (SA); Khalil Ibrahim Khalil, Faiyum (EG); Samah Ahmed Abd-El Twab Awad, Faiyum (EG); Amany Ahmed Abd-El Halim Mohamed, Faiyum (EG)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/925,150

(22) Filed: Oct. 24, 2024

Related U.S. Application Data

(63) Continuation of application No. 18/792,498, filed on Aug. 1, 2024.

(51) Int. Cl.
| | |
|---|---|
| D01F 8/18 | (2006.01) |
| A23B 2/733 | (2025.01) |
| A61L 2/00 | (2006.01) |
| A61L 2/232 | (2006.01) |
| C02F 1/50 | (2023.01) |
| A61L 101/32 | (2006.01) |

(52) U.S. Cl.
CPC ............ *A23B 2/733* (2025.01); *A61L 2/0082* (2013.01); *A61L 2/232* (2013.01); *C02F 1/50* (2013.01); *A61L 2101/32* (2020.08); *A61L 2202/24* (2013.01); *C02F 2303/04* (2013.01)

(58) Field of Classification Search
CPC ....... A23B 2/733; A61L 2/0082; A61L 2/232; A61L 2101/32; A61L 2202/24; C02F 1/50; C02F 2303/04
USPC ......................................................... 426/335
See application file for complete search history.

(56) References Cited

U.S. PATENT DOCUMENTS

2021/0230777 A1* 7/2021 Reed .................. C08G 73/0266

FOREIGN PATENT DOCUMENTS

| CN | 108752610 B | 12/2020 |
|---|---|---|
| CN | 116998502 A | 11/2023 |

(Continued)

OTHER PUBLICATIONS

Natasa Jokovic, et al; "Onion Peel as a Potential Source of Antioxidants and Antimicrobial Agents"; Agronomy 2024, 14, 453, pp. 1-16.

(Continued)

*Primary Examiner* — Brent T O'Hern
(74) *Attorney, Agent, or Firm* — Oblon, McClelland, Maier & Neustadt, L.L.P.

(57) ABSTRACT

A food preservative having antimicrobial and antioxidant activity and a method of fabrication. The food preservative includes an inner core including an extract of pomegranate pools and onion pools, and an outer coating of chia nano particles. The outer costing encapsulates the inner core.

9 Claims, 17 Drawing Sheets

(56) References Cited

FOREIGN PATENT DOCUMENTS

| | | |
|---|---|---|
| IN | 238970 B | 3/2010 |
| IN | 202211027664 | 6/2023 |

OTHER PUBLICATIONS

Seah Jia Min, et al., "Development of edible chitosan film incorporated with Pomegranate peel extract for the packaging of beef", Malaysian Journal of Analytical Sciences, vol. 25, Issue 3, 2021, p. 532-545.

Md Morshedur Rahman, "Sustainable chitosan biomordant dyeing and functionalization of cotton fabrics using pomegranate rind and onion peel extracts", Journal of Natural Fibers 2024, vol. 21, Issue 1, Dec. 7, 2023.

\* cited by examiner

NATURAL FOOD PRESERVATIVE

CROSS REFERENCE TO RELATED APPLICATIONS

This application is a continuation U.S. patent application Ser. No. 18/792,498, filed on Aug. 8, 2024, the entire contents of which are incorporated herein by reference.

BACKGROUND

Technical Field

The present disclosure is directed to a food preservative and, more particularly, towards a food preservative derived from pomegranate/onion peel extracts and nanoencapsulated in chia seeds.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Food preservatives are substances primarily added to processed foods or other foods produced on an industrial scale to improve safety, increase the shelf life, and decrease deterioration of the food product by bacteria or oxidation. Synthetic additives are widely used as food preservatives; however, these additives may have an adverse impact on the health of the consumer, requiring a need for safe, natural sources as alternatives to synthetic additives.

Natural additives are chemical compounds extracted from plants, animals, or minerals. Examples of natural preservative include plant extracts, chitosan, bacteriocins, bioactive peptides, and essential oils.

Although a few natural additives have been developed as food preservatives, challenges such as solubility, sensorial properties, and instability during food processing hinder their use as food additives. Therefore, an objective of the present disclosure is to obtain a natural food preservative showing improved antimicrobial and antioxidant properties.

SUMMARY

In an exemplary embodiment, a food preservative having antimicrobial and antioxidant activity is described. The food preservative comprises of an inner core comprising an extract of at least one of pomegranate peels and onion peels and an outer coating comprising chia seed nanoparticles. The outer coating encapsulates the inner core.

In some embodiments, the food preservative has a half maximal inhibitory concentration ($IC_{50}$) of 3.00 milligram per milliliter (mg/mL) or less against *Staphylococcus aureus* gram-positive bacteria.

In some embodiments, the food preservative has an antimicrobial inhibition rate of 70% or greater against *Staphylococcus aureus* gram-positive bacteria.

In some embodiments, the food preservative is in the form of a powder having an average particle size of 100 nanometers (nm) or less.

In some embodiments, the food preservative is in the form of nanoparticles having a smooth surface with a plurality of protrusions.

In some embodiments, the food preservative is in the form of nanoparticles having a rough surface with a plurality of pores. In some embodiments, the pores have an average diameter of 35 nm or less.

In some embodiments, at least one of the inner core and the outer coating comprises crystallites with a crystallite size of at least 35 Angstroms (Å).

In some embodiments, the food preservative has a basal spacing of at least 4 Å.

In another exemplary embodiment, a method of fabricating the food preservative is described. The method comprises preparing the extract of at least one of pomegranate peels and onion peels, and then combining a nonionic surfactant and the extract to obtain a reaction mixture. The method further comprises adding ground chia seeds to the reaction mixture and drying the reaction mixture to obtain the food preservative.

In some embodiments, the nonionic surfactant is selected from the group consisting of a polyoxyethylenated alkylphenol, a polyoxyethylenated alcohol, an alkyl ether, a sorbitan fatty acid ester, a polyoxyethylene fatty acid ester, and a sorbitan monostearate. In some embodiments, the nonionic surfactant is polysorbate 80.

In some embodiments, the method further comprises grinding the chia seeds to obtain ground chia seeds. The ground chia seeds have an average particle size of less than 100 nm.

In some embodiments, the method further comprises washing at least one of a pomegranate peel or an onion peel, then drying to obtain a dried bioactive material. The pomegranate peel or the onion peel are dried at a temperature of 20 to 60° C. for 1 to 3 hours (h). The method further comprises grinding the dried bioactive material to obtain a bioactive powder, and then preparing the extract from the bioactive powder with a polar protic solvent.

In some embodiments, the polar protic solvent is selected from the group consisting of water, ethanol, methanol, ammonia, acetic acid, and hydrogen fluoride. In some embodiments, the polar protic solvent is ethanol.

In yet another embodiment, a method of inhibiting a growth of at least one bacterium and/or at least one fungus is described. The method comprises adding the food preservative to a food product. The bacterium is selected from the group consisting of a gram-positive bacterium and a gram-negative bacterium. The fungus is selected from the group consisting of a yeast, a mold, and a saprotroph. In some embodiments, the bacterium is selected from the group consisting of *Staphylococcus aureus* (*S. aureus*), *Bacillus cereus* (*B. cereus*), *Salmonella typhimurium* (*S. tymphimurium*), and *Escherichia coli* (*E. coli*). In some embodiments, the fungus is selected from *Pencillium reqfortii* (*P. reqfortii*), *Aspergillus niger* (*A. niger*), and *Candida albicans* (*C. albicans*).

In an exemplary embodiment, a method of reducing *Staphylococcus aureus* biofilm formation is further described. The method comprises inhibiting the initial adhesion phase of the biofilm by contacting the food preservative to a surface. The surface is selected from a group consisting of a living tissue surface, an indwelling medical device surface, an industrial or potable water system pipe surface, and a natural aquatic system surface.

BRIEF DESCRIPTION OF THE SEVERAL VIEWS OF THE DRAWING(S)

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
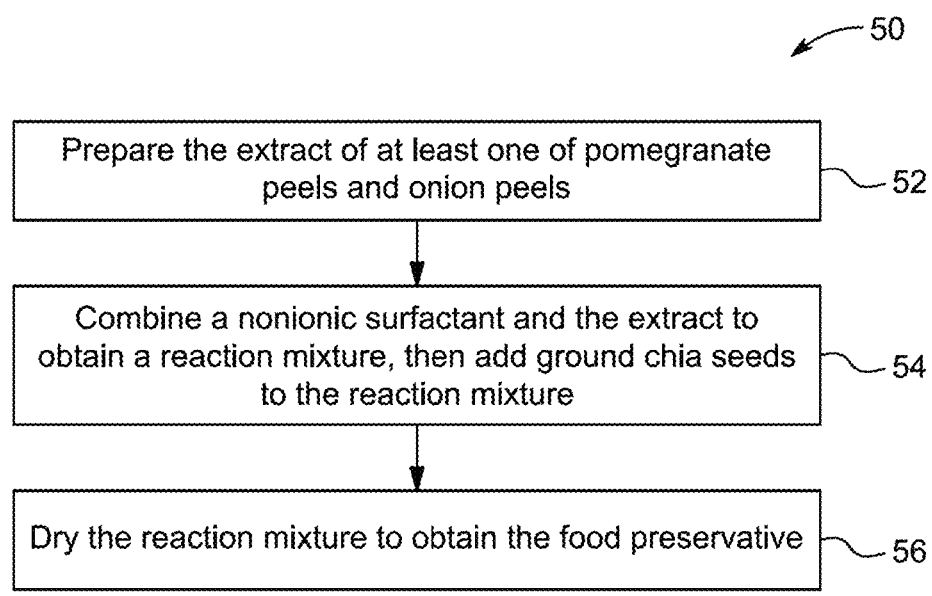
FIG. 1A is a flowchart illustrating a method of preparing a food preservative, according to certain embodiments.

In the drawings, reference numerals designate identical or corresponding parts throughout the several views. Further, as used herein, the words "a," "an" and the like generally carry a meaning of "one or more," unless stated otherwise.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, the term "preservative" refers to a natural or artificial chemical that is added to a varied range of products, such as food products, beverages, pharmaceutical drugs, paints, cosmetics, wood, etc., to prevent deterioration by microbial growth or undesirable chemical changes.

As used herein, "crystallites" refers to microscopic crystals that are bonded together by boundaries that are substantially irregular, including polycrystalline solids.

As used herein, the term "biofilm" refers to a population of microorganisms concentrated at an interface, usually a solid or liquid, and typically surrounded by an extracellular polymeric slime matrix. Biofilms may form on living or non-living surfaces in natural, industrial, and hospital settings. Biofilms can contain many different microorganisms, e.g., bacteria, archaea, protozoa, fungi, and algae.

As used herein, "ash content" refers to a measure of the amount of minerals and other inorganic materials that remain after a sample has been entirely burned. The ash content indicates the incombustible component.

The present disclosure describes a food preservative comprising an inner core comprising an extract of at least one of pomegranate peels and onion peels and an outer coating comprising chia seed nanoparticles. The chia seeds encapsulate the extracts of the pomegranate peel and/or onion peel, resulting in a preservative that possess antioxidant and antimicrobial characteristics. The food preservative is in the form of a particulate, preferably a nanoparticle, in powder form.

The food preservative comprises an inner core comprising an extract of a pomegranate peel and/or an onion peel. In a preferred embodiment, the inner core comprises the extract of the peel of a pomegranate. In another embodiment, the inner core comprises the extract of the peel of an onion. In some embodiments, the inner core comprises the extract of the peel of a pomegranate and the extract of the peel of an onion.

Onion peels may be a rich source of essential nutrients such as proteins and carbohydrates. The peel of the onion may be obtained from any onion variety, such as a yellow onion, a red onion, a sweet onion, a white onion, a shallot, a green onion, or a combination thereof. In one embodiment, the onion peel has a moisture content of about 9 to 10%, a protein content of about 1 to 3%, a fat content of about 1 to 2.5%, an ash content of about 8 to 10%, and a carbohydrate content of about 65 to 70%. In another embodiment, the onion peel has a moisture content of about 9.57%±0.01, a protein content of about 2.01%±0.01, a fat content of about 1.92%±0.01, an ash content of about 9.2%±0.01, a fiber content of about 8.79%±0.01, and a carbohydrate content of about 68.51%±0.01.

Onion peels may also be a rich source of bioactive compounds, such as phenols and flavonoids. In one embodiment, the extract of the onion peel comprises at least one selected from the group consisting of a phenol and a flavonoid. In one embodiment, the extract of the onion peel comprises a phenol. In another embodiment, the extract of the onion peel comprises a flavonoid. In yet another embodiment, the extract of the onion peel comprises a phenol and a flavonoid. In an embodiment, the extract of the onion peel has a phenol content of about 100 to 300 mg gallic acid equivalents per gram of dry weight (mg GAE/g DW), preferably 110 to 290 mg GAE/g DW, preferably 120 to 280 mg GAE/g DW, preferably 130 to 270 mg GAE/g DW, preferably 140 to 260 mg GAE/g DW, preferably 150 to 250 mg GAE/g DW, preferably 160 to 240 mg GAE/g DW, preferably 160 to 230 mg GAE/g DW, preferably 160 to 220 mg GAE/g DW, preferably 160 to 210 mg GAE/g DW, preferably 160 to 200 mg GAE/g DW, preferably 160 to 190 mg GAE/g DW, preferably 160 to 180 mg GAE/g DW, preferably 160 to 170 mg GAE/g DW, most preferably about 167.09 mg GAE/g DW. In an embodiment, the onion peel has a flavonoid content in the range of 50 to 150 mg Quercetin equivalents per gram of dry weight (mg QE/g DW), preferably 60 to 140 mg QE/g DW, preferably 70 to 130 mg QE/g DW, preferably 80 to 120 mg QE/g DW, preferably 90 to 110 mg QE/g DW, preferably 90 to 100 mg QE/g DW, most preferably 96.03 mg QE/g DW. In one embodiment, the extract of an onion peel further comprises at least one organic component selected from the group consisting of a gallic acid, a chlorogenic acid, a catechin, a methyl gallate, a rutin, an ellagic acid, a coumaric acid, a vanillin, a ferulic acid, a naringenin, a daidzein, a syringic acid, a quercetin, a cinnamic acid, an apigenin, and a kaempferol. In one embodiment, the organic component is at least one selected from the group consisting of a chlorogenic acid, a syringic aid, a quercetin, a coumaric acid, a rutin, a vanillin, and a ferulic acid. In one embodiment, the extract of the onion peel comprises a chlorogenic acid in an amount of 800 to 1200 µg/g, preferably 820 to 1180 µg/g, preferably 840 to 1160 µg/g, preferably 860 to 1140 µg/g, preferably 880 to 1120 µg/g, preferably 900 to 1100 µg/g, preferably 920 to 1080 µg/g, preferably 920 to 1040 µg/g, preferably 920 to 1020 µg/g, most preferably 937.94 to 1003.28 µg/g. In one embodiment, the extract of the onion peel comprises a syringic acid in an amount of 800 to 1200 µg/g, preferably 820 to 1180 µg/g, preferably 840 to 1160 µg/g, preferably 860 to 1140 µg/g, preferably 880 to 1120 µg/g, preferably 900 to 1100 µg/g, preferably 920 to 1080 µg/g, preferably 920 to 1040 µg/g, preferably 920 to 1020 µg/g, most preferably 937.94 to 1003.28 µg/g. In one embodiment, the extract of the onion peel comprises quercetin in an amount of 800 to 1200 µg/g, preferably 820 to 1180 µg/g, preferably 840 to 1160 µg/g, preferably 860 to 1140 µg/g, preferably 880 to 1120 µg/g, preferably 900 to 1100 µg/g, preferably 920 to 1080 µg/g, preferably 920 to 1040 µg/g, preferably 920 to 1020 µg/g, most preferably 937.94 to 1003.28 µg/g. In one embodiment, the extract of the onion peel comprises a coumaric acid in an amount of 10 to 40 µg/g, preferably 11 to 39 µg/g, preferably 12 to 38 µg/g, preferably 13 to 37 µg/g, preferably 14 to 36 µg/g, preferably 15 to 35 µg/g, preferably 16 to 34 µg/g, preferably 17 to 33 µg/g, preferably 18 to 32 µg/g, preferably 19 to 31 µg/g, preferably 20 to 30 µg/g, preferably 21 to 29 µg/g, preferably 22 to 29 µg/g, preferably 23 to 29 µg/g, preferably 24 to 29 µg/g, preferably 25 to 29 µg/g, preferably 26 to 29 µg/g, preferably 27 to 29 µg/g, preferably 28 to 29 µg/g, most preferably 28.63 µg/g. In one embodiment, the extract of the onion peel comprises rutin in an amount of 1 to 10 µg/g, preferably 2 to 9 µg/g, preferably 3 to 8 µg/g, preferably 3 to 7 µg/g, preferably 3 to 6 µg/g, preferably 3 to 5 µg/g, preferably 3 to 4 µg/g, most preferably 3.13 µg/g. In one embodiment, the extract of the onion peel comprises vanillin in an amount of 1 to 10 µg/g, preferably 2 to 9 µg/g, preferably 2 to 8 µg/g, preferably 2 to 7 µg/g, preferably 2 to 6 µg/g, preferably 2 to 5 µg/g, preferably 2 to 4 µg/g, preferably 2 to 3 µg/g, most preferably 2.92 µg/g. In one embodiment, the extract of the onion peel comprises a ferulic acid in an amount of 10 to 40 µg/g, preferably 11 to 39 µg/g, preferably 12 to 38 µg/g, preferably 13 to 37 µg/g, preferably 14 to 36 µg/g, preferably 15 to 35 µg/g, preferably 16 to 34 µg/g, preferably 17 to 33 µg/g, preferably 18 to 32 µg/g, preferably 19 to 31 µg/g, preferably 20 to 30 µg/g, preferably 21 to 29 µg/g, preferably 22 to 28 µg/g, preferably 23 to 27 µg/g, preferably 23 to 26 µg/g, preferably 23 to 25 µg/g, preferably 23 to 24 µg/g, most preferably 23.27 µg/g.

Pomegranate peels may also be a rich source of essential nutrients such as proteins and carbohydrates. In one embodiment, the pomegranate peel has a moisture content of about 5 to 20%, a protein content of about 1 to 8%, a fat content of about 1 to 10%, an ash content of about 1 to 8%, and a carbohydrate content of about 60 to 75%. In another embodiment, the pomegranate peel has a moisture content of about 12.23%±0.01, a protein content of about 2.33%±0.01, a fat content of about 2.60%±0.01, an ash content of about 3.56%±0.01, fiber content of about 12.10%±0.01, and carbohydrate content of about 67.09%±0.01.

Pomegranate peels are also rich in bioactive compounds such as phenols and flavonoids. In one embodiment, the extract of the pomegranate peel comprises at least one selected from the group consisting of a phenol and a flavonoid. In one embodiment, the extract of the pomegranate peel comprises a phenol. In another embodiment, the extract of the pomegranate peel comprises a flavonoid. In yet another embodiment, the extract of the pomegranate peel comprises a phenol and a flavonoid. In an embodiment, the extract of the pomegranate peel has a phenol content of about 100 to 400 mg GAE/g DW, preferably 110 to 390 mg GAE/g DW, preferably 120 to 380 mg GAE/g DW, preferably 130 to 370 mg GAE/g DW, preferably 140 to 360 mg GAE/g DW, preferably 150 to 350 mg GAE/g DW, preferably 160 to 340 mg GAE/g DW, preferably 170 to 330 mg GAE/g DW, preferably 180 to 320 mg GAE/g DW, preferably 190 to 310 mg GAE/g DW, preferably 200 to 300 mg GAE/g DW, preferably 210 to 290 mg GAE/g DW, preferably 220 to 280 mg GAE/g DW, preferably 230 to 270 mg GAE/g DW, preferably 240 to 260 mg GAE/g DW, preferably 250 to 260 mg GAE/g DW, most preferably about 257.81 mg GAE/g DW. In an embodiment, the onion peel has a flavonoid content in the range of 50 to 150 mg QE/g DW, preferably 60 to 140 mg QE/g DW, preferably 70 to 130 mg QE/g DW, preferably 80 to 120 mg QE/g DW, preferably 90 to 120 mg QE/g DW, preferably 110 to 120 mg QE/g DW, most preferably 112.32 mg QE/g DW. In one embodiment, the extract of the pomegranate peel further comprises at least one organic component selected from the group consisting of a gallic acid, a chlorogenic acid, a catechin, a methyl gallate, a rutin, an ellagic acid, a coumaric acid, a vanillin, a ferulic acid, a naringenin, a daidzein, a syringic acid, a quercetin, a cinnamic acid, an apigenin, and a kaempferol. In one embodiment, the organic component is at least one selected from the group consisting of a chlorogenic acid, a catechin, a methyl gallate, a coffee acid, a syringic acid, an ellagic acid, a vanillin, a ferulic acid, a naringenin, a daidzein, and quercetin. In one embodiment, the extract of the pomegranate peel comprises a coffee acid in an amount of 10 to 70 µg/g, preferably 20 to 60 µg/g, preferably 30 to 60 µg/g, preferably 40 to 60 µg/g, preferably 50 to 60 µg/g, most preferably 54.91 µg/g. In one embodiment, the extract of the pomegranate peel comprises vanillin in an amount of 5 to 70 µg/g, preferably 10 to 65 µg/g, preferably 15 to 60 µg/g, preferably 20 to 55 µg/g, preferably 25 to 50 µg/g, preferably 30 to 45 µg/g, preferably 35 to 40 µg/g, most preferably 37.58 µg/g. In one embodiment, the extract of the onion peel comprises a ferulic acid in an amount of 80 to 100 µg/g, preferably 81 to 99 µg/g, preferably 82 to 98 µg/g, preferably 83 to 97 µg/g, preferably 84 to 96 µg/g, preferably 85 to 95 µg/g, preferably 86 to 94 µg/g, preferably 87 to 93 µg/g, preferably 88 to 93 µg/g, preferably 89 to 93 µg/g, preferably 90 to 93 µg/g, preferably 91 to 93 µg/g, preferably 92 to 93 µg/g, most preferably 92.03 µg/g.

In one embodiment, the onion peel may be the outer peel, the inner peel, or a combination thereof. In one embodiment, after peeling the pomegranate or onion, the peels are subjected to an extraction method to obtain the extract. Any suitable extraction method and extraction solvent may be used. Suitable extraction solvents may be water, ethanol, acetone, methanol, acetonitrile, dimethyl sulfoxide (DMSO), chloroform, n-hexane, ethyl acetate, toluene, dichloromethane (DCM), isopropanol, or any other suitable extraction solvent. In one embodiment, the extraction solvent is ethanol, preferably 50% ethanol, preferably 55% ethanol, preferably 60% ethanol, preferably 65% ethanol, most preferably 70% ethanol. Although the description herein provided refers to the use of peels of pomegranate or onion, it may be understood by a person skilled in the art that the extract may also include any other constituents of pomegranate or onion—for example, the seed, juice, or any other plant parts.

The inner core is encapsulated with an outer coating, comprising chia seed nanoparticles. Chia seeds may contain essential nutrients such as polyunsaturated fatty acids, dietary fiber, proteins, vitamins, and minerals. Chia seeds may also be a rich source of bioactive compounds such as polyphenols and antioxidants. Chia seeds may further comprise at least one organic component selected from the group consisting of a caffeic acid, a chlorogenic acid, quercetin, a rosmarinic acid, a gallic acid, a cinnamic acid, myricetin, and kaemferol. Further, chia seeds may be a rich source of isoflavones, such as daidzein, glycitein, and genistein. In one embodiment, the chia seeds have a protein content of about 10 to 30%, a fat content of about 25 to 35%, a carbohydrate content of about 15 to 55%, and a dietary fiber content of about 10 to 40%.

In some embodiments, the chia seed nanoparticles may be derived from chia seed mucilage. Chia seed nanoparticles show high solubility in food, facilitating its incorporation into the food. Various nanoencapsulation techniques known in the art may be adopted to encapsulate the inner core within the chia seed nanoparticles. In an embodiment, the food preservative is the extract of the onion peel encapsulated by the chia seed nanoparticles. In another embodiment, the food preservative is the extract of the pomegranate peel encapsulated by the chia seed nanoparticles. In another embodiment, the food preservative is a mixture of the extract of the pomegranate peel and the onion peel encapsulated by the chia seed nanoparticles.

In one embodiment, the extract may be a liquid form or a solid form. In some embodiments, a solid form of the extract may be made by lyophilizing the liquid extract of the present invention. In another embodiment, the extract is in the form of a powder. In some embodiments, the food preservative is a powder with an average particle size of 100 nm or less. In another embodiment, the food preservative is in the form of nanoparticles with a smooth surface and a plurality of protrusions. In one embodiment, the food preservative is in the form of nanoparticles with a rough surface with several pores. In some embodiments, the pores on the surface of the food preservative nanoparticles have an average diameter of 35 nm or less.

In one embodiment, the food preservative is crystalline with at least one of the inner core and the outer coating comprising crystallites. In some embodiments, the crystallites have a crystallite size of at least 30 Å, preferably at least 31 Å, preferably at least 32 Å, preferably at least 33 Å, preferably at least 34 Å, preferably at least 35 Å, most preferably at least 36 Å. The food preservative has a basal spacing of at least 2 Å, preferably at least 2.5 Å, preferably at least 3 Å, preferably at least 3.5 Å, preferably at least 4 Å, most preferably at least 4.2 Å.

The food preservative is effective against gram-positive and gram-negative bacteria, fungi, and yeast. In some embodiments, the food preservative has a half maximal inhibitory concentration ($IC_{50}$) of 3.50 mg/mL or less, preferably 3 mg/mL or less against *Staphylococcus aureus* gram-positive bacteria. In some embodiments, the food preservative has an antimicrobial inhibition rate of 70% or greater, preferably 71% or greater, preferably 72% or greater, preferably 73% or greater, preferably 74% or greater, preferably 75% or greater, preferably 76% or greater, preferably 77% or greater, preferably 78% or greater, preferably 79% or greater, most preferably 80% or greater against *Staphylococcus aureus* gram-positive bacteria. In some embodiments, when the food preservative has an antimicrobial inhibition rate of 70% or greater, preferably 71% or greater, preferably 72% or greater, preferably 73% or greater, preferably 74% or greater, preferably 75% or greater, preferably 76% or greater, preferably 77% or greater, preferably 78% or greater, preferably 79% or greater, most preferably 80% or greater against *B. cereus, C. albicans, A. niger,* and *P. reqfortii*. In some embodiments, the food preservative shows antibacterial activity better than commercially used penicillin and ampicillin.

Figure 1B:
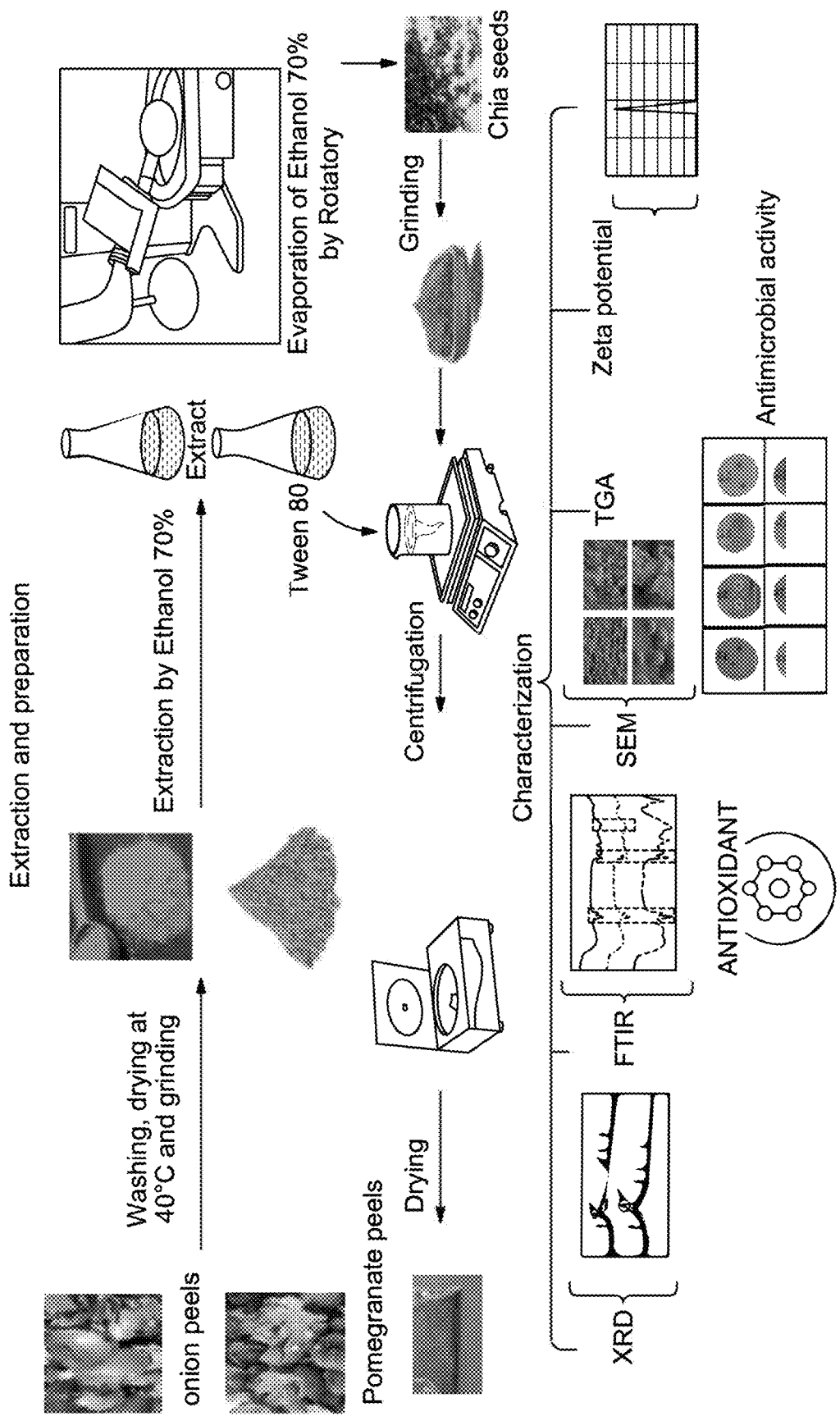
FIG. 1B is a schematic illustration depicting the preparation and characterization of onion peel extract encapsulated in chitosan seed nanoparticles (OPE-CSNP), and pomegranate peel extract encapsulated in chitosan seed nanoparticles (PPE-CSNP), according to certain embodiments.

A second aspect of the present disclosure is a method of fabricating food preservatives. FIG. 1A illustrates a schematic flow chart of a method 50 of fabricating the food preservative. A schematic illustration depicting its fabrication is provided in FIG. 1B. FIG. 1A and FIG. 1B may be read in tandem. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 comprises preparing the extract of at least one of pomegranate peels and onion peels. In an embodiment, the method comprises preparing an extract of the pomegranate peels. In another embodiment, the method comprises preparing an extract of the onion peels. In yet another embodiment, the method comprises preparing an extract of the pomegranate and onion peels. The extract is prepared by obtaining peels of onion and pomegranate. The peels are then washed with a solvent to remove impurities. In one embodiment, the solvent is water. Any suitable water may be used such as tap water, distilled water, bi-distilled water, deionized water, deionized distilled water, and reverse osmosis water. In one embodiment, the peels are washed with distilled water. After washing, the pomegranate peel and/or the onion peel are dried at 20 to 60° C., preferably 30 to 50° C., preferably 30° C. for 1 to 3 h to obtain a dried bioactive material. The drying temperature and time may vary depending on the moisture content in the peel. In an embodiment, the pomegranate peel and/or the onion peel may be dried in an oven or air dried at room temperature. The dried bioactive material has a moisture content of less than 30%, preferably 25%, preferably 20%, preferably 15%, and preferably 10% based on the total weight of the dried bioactive material. After drying, the dried bioactive material is ground to obtain a bioactive powder. In an embodiment, the dried bioactive material can be crushed using ball-milling or any other suitable grinding method to obtain the bioactive powder. The bioactive powder is an ultra-fine powder. In one embodiment, the ultra-fine powder has an average particle size of 100 nm or less. The bioactive powder is further treated with a polar protic solvent to obtain the extract. Suitable examples of the polar protic solvent include, but are not limited to, water, ethanol, methanol, ammonia, acetic acid, and hydrogen fluoride. In one embodiment, the polar protic solvent is ethanol, preferably 50% ethanol, preferably 55% ethanol, preferably 60% ethanol, preferably 65% ethanol, most preferably 70% ethanol. The extract may be further dried using a drying appliance, such as a rotary drier, an oven, and the like.

At step 54, optional, the method 50 comprises combining a nonionic surfactant and the extract to obtain a reaction mixture, then adding ground chia seeds to the reaction mixture. The nonionic surfactant is selected from the group consisting of a polyoxyethylenated alkylphenol, a polyoxyethylenated alcohol, an alkyl ether, a sorbitan fatty acid ester, a polyoxyethylene fatty acid ester, and a sorbitan monostearate. In one embodiment, the nonionic surfactant is polysorbate 80. In some embodiments, the nonionic surfactant may be dissolved in an organic solvent before combining the nonionic surfactant and the extract. In one embodiment, the organic solvent is selected from the group consisting of acetone, ethyl acetate, hexane, heptane, dichloromethane, methanol, ethanol, tetrahydrofuran, acetonitrile, dimethylformamide, toluene, and DMSO. In one embodiment, the organic solvent is ethanol.

In some embodiments, the ground chia seeds are added to the extract. In an embodiment, the chia seeds can be crushed using ball-milling or any other suitable grinding method to obtain the ground chia seeds. The ground chia seeds are in the form of an ultra-fine powder. In one embodiment, the ground chia seeds have an average particle size of 100 nm or less.

At step 56, the method 50 comprises drying the reaction mixture to obtain the food preservative. In an embodiment, the reaction mixture is dried to a temperature sufficient enough to remove moisture without damaging or destroying the nutrients in the food preservative. In one embodiment, the reaction mixture is dried at a temperature of 20 to 60° C., preferably 30 to 50° C., preferably 30° C. for 1 to 3 h to obtain the food preservative.

In one embodiment, the food preservative is used to prevent the deterioration of a food product over time. The deterioration may be caused by increased bacteria presence and/or oxidation. The food products may include, but are not limited to, perishable foods and beverages such as meat, poultry, fish, dairy products, juices, fresh produce, frozen foods, frozen snacks, and baked goods such as cookies, cereal, and nutrition bars. In some embodiments, a method of inhibiting the growth of at least one bacterium and/or at least one fungus using the food preservative is described. The bacterium can be a gram-positive and/or gram-negative bacteria group, and the fungus is at least one of yeast, mold, and saprotroph. In an embodiment, the bacteria is at least one of *S. aureus, B. cereus, S. tymphimurium*, and *E. coli*, and the fungus is at least one of *C. albicans, A. niger*, and *P. reqfortii*. In some embodiments, the growth of bacterium or fungi is reduced, minimized, and/or prevented by adding the food preservative to a food product.

A method of reducing an *S. aureus* biofilm formation is described. The method includes contacting the food preservative with a surface. Upon contacting the surface, the food preservative inhibits or kills the growth of at least one bacterium and/or at least one fungus by inhibiting its initial adhesion phase, thereby protecting the surface from biofilm formation and/or accumulation. In some embodiments, the surface is selected from a group consisting of a living tissue surface, a liquid surface, an industrial or potable water system pipe surface, a natural aquatic system surface, and an indwelling medical device surface. The surface may also refer to the interior or exterior of pipes, for example, drains, swimming pools, tanks (e.g., for aquaculture), purification filters, toilet bowls, sinks, and greenhouse surfaces. It also includes liquid surfaces, such as water from a drinking trough. In some embodiments, the surface is of an indwelling medical device, such as a prosthetic, a mechanical heart valve, a cardiac pacemaker, an arteriovenous shunt, a schleral buckle, catheters, tympanostomy tube, a tracheostomy tube, a surgical suture, a bone anchor, a bone screw, an intraocular lens, a contact lens, an intrauterine device, an aortofemoral graft, and a vascular graft.

EXAMPLES

The following examples demonstrate a food preservative as described herein. The examples are provided solely for illustration and are not to be construed as limitations of the present disclosure, as many variations are possible without departing from the spirit and scope of the present disclosure.

Example 1: Chemical Composition of Onion Peel (OP) and Pomegranate Peel (PP)

Both OP and PP were evaluated for moisture content, protein, fat, ash, fiber, and percentage of carbohydrates. They were also computed for their energy value. The moisture content of PP was higher at 12.23% than that of OP, at 9.57%. The protein was estimated to be higher in PP than OP by a small margin, with the protein in an amount of 2.33 and 2.01%, respectively. The percentage of fat in PP was found to be higher than in OP, with the fat in an amount of 2.60 and 1.92%, respectively. The onion and pomegranate peels were burned in a Muffle Furnace at 550° C. to completely burn the peels and evaluate the remaining inorganic materials. The percentage of ash was higher in OP than in PP by approximately three times, the amount of ash being 9.20 and 3.56%, respectively. The fiber content was higher in PP than OP, with the amount of fiber being 12.10 and 8.79%, respectively. It was found that the carbohydrate content was higher in OP compared to PP, the amount of carbohydrates being 68.51 and 67.09%, respectively. Finally, the amount of energy present in PP, 301.08 cal/100 g, was higher than that of OP, 299.36 cal/100 g. The results of these tests are illustrated in Table 1.

TABLE 1

Chemical composition of OP and PP

| Parameter | OP | PP |
| --- | --- | --- |
| Moisture % | 9.57 | 12.32 |
| Crude protein | 2.01 | 2.33 |
| Crude fat | 1.92 | 2.60 |
| Total fiber | 8.79 | 12.10 |
| Ash | 9.20 | 3.56 |
| Carbohydrates | 68.51 | 67.09 |
| Energy value | 299.36 | 301.08 |

Example 2: Extraction Yield of OP, PP, Onion Peel Extract-Chia Seed Nanoparticle (OPE-CSNP) and Pomegranate Peel-Chia Seed Nanoparticle (PPE-CCSNP)

Figure 2A:
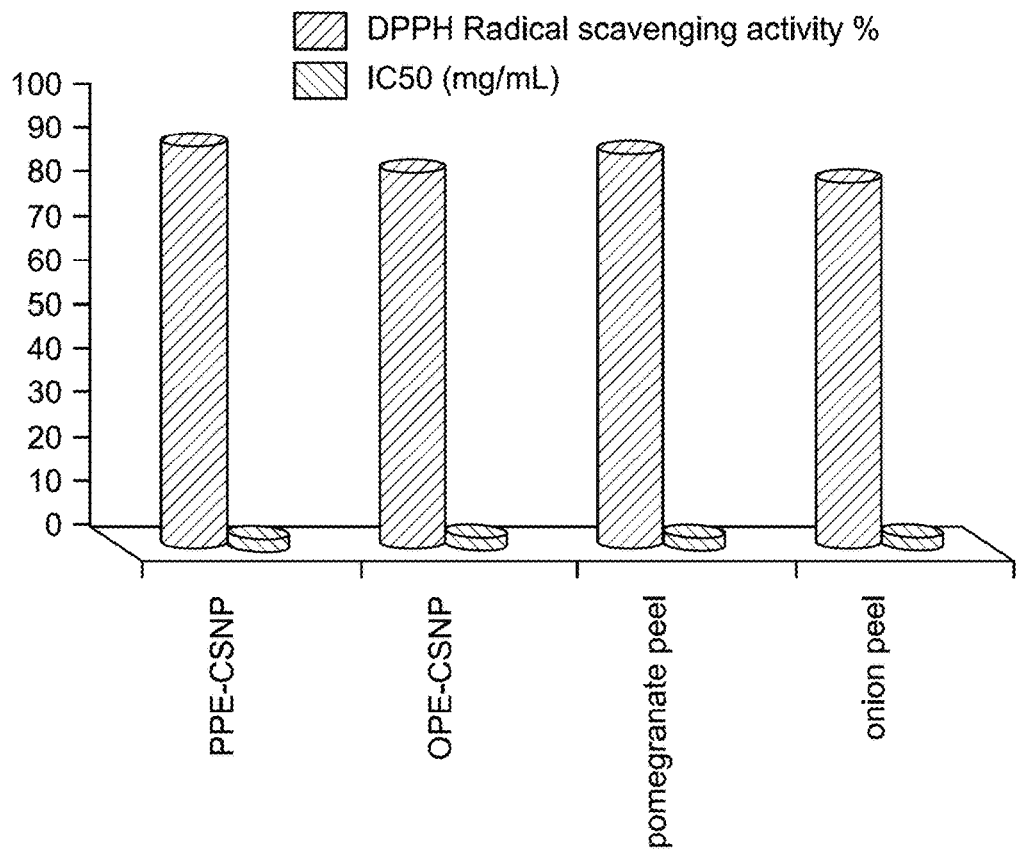
FIG. 2A shows the antioxidant scavenging activity by (2,2-diphenyl-1-picrylhydrazyl) (DPPH %) and half maximal inhibitory concentration ($IC_{50}$) values of onion peel extract (OPE), pomegranate peel extract (PPE), OPE-CSNP, and PPE-CSNP, according to certain embodiments.
Figure 2B:
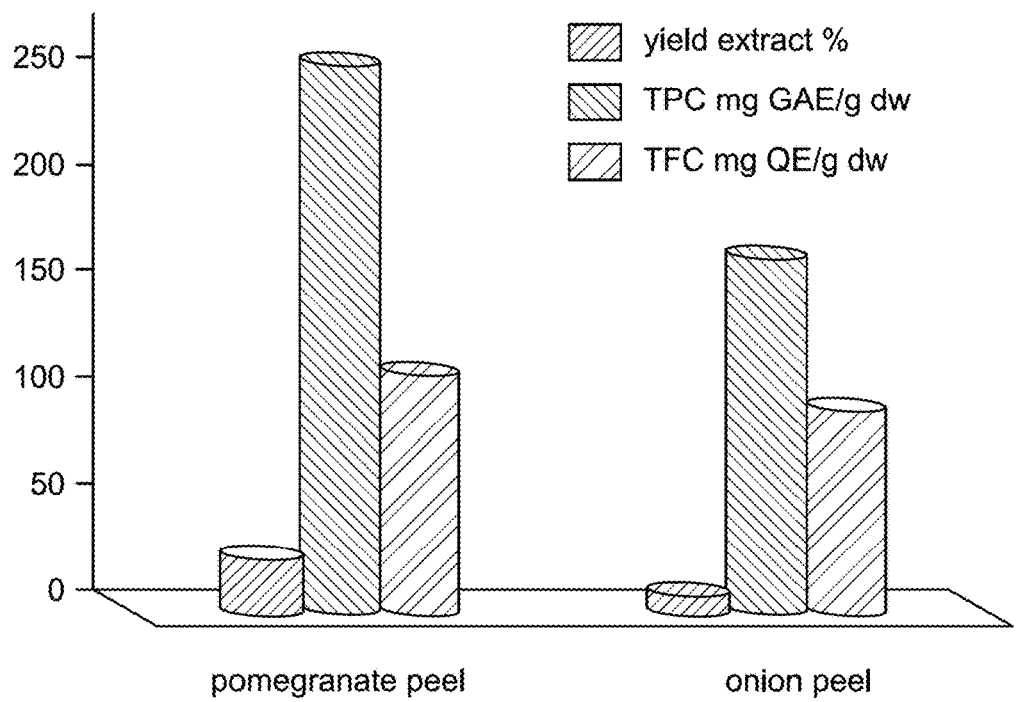
FIG. 2B shows the percentage yield extract, total phenol content (TPC), and total flavonoid content (TFC) of onion peel and pomegranate peel, according to certain embodiments.

Table 2 shows the amount of waste material that was extracted. Different quantities of extractable soluble bioactive compounds are indicated by the 70% aqueous ethanol extraction yield in PP, which was 26.23%, while OP was 8.87%. PP's high yield extract percentage (26.23%) indicates that it is a useful source of bioactive substances (FIG. 2B). The OP extraction yield concentration of 8.87% also indicates that it is a useful source of bioactive substances.

TABLE 2

Proximate analysis, yield, TPC, TFC, and antioxidant scavenging activity (DPPH %, $IC_{50}$) of OPE, PPE, OPE-CSNPs, and PPE-CSNPs.

| Parameter | OPE | PPE | OPE-CSNPs | PPE-CSNPs |
| --- | --- | --- | --- | --- |
| Yield extract % | 8.87 | 26.23 | — | — |
| TPC mg GAE/g DW | 167.09 | 257.81 | — | — |
| TFC mg QE/g DW | 96.03 | 112.32 | — | — |
| DPPH Radical Scavenging activity % | 83.32 | 89.55 | 85.27 | 91.34 |
| $IC_{50}$ (mg/mL) | 3.00 | 2.80 | 2.93 | 2.64 |

Example 3: Measurement of Total Phenol Contents (TPC) and Total Flavonoid (TFC) Content in PPE and OPE Results in Table 2 showed that the total phenols were higher in the PP extract than the OP extract, measured at 257.81 and 167.09 mg GAE/g DW, respectively. Table 3 showed that the amount of flavonoid in PPE, at 112.32 mg QE/g DW, was higher than OPE, at 96.03 mg QE/g DW, when extracted with 70% ethanol (FIG. 2B).

Example 4: 2,2-Diphenyl-1-Picrylhydrazyl (DPPH) Radical Scavenging Activity

The antioxidant capability of synthetic and plant extracts is assessed through the DPPH assay, which measures the ability of these compounds to reduce the stable free radical DPPH. As seen in Table 2 and FIG. 2A, the PPE had the highest level of inhibition (89.55%) compared to the OPE, which produced an inhibition rate of 83.32%. Because of this, the $IC_{50}$ found in OPE was higher than in PPE. The $IC_{50}$ for PPE and OPE are 2.80 mg/mL and 3.00 mg/mL, respectively. The rate of inhibition in PPE-CSNP (91.34%) was higher than that in OPE-CCSNP (85.27%) indicating an increase in antioxidant activity. The $IC_{50}$ for OPE-CCSNP (2.93 mg/mL) was higher than that for PPE-CSNP (2.64 mg/mL).

Figure 3A:
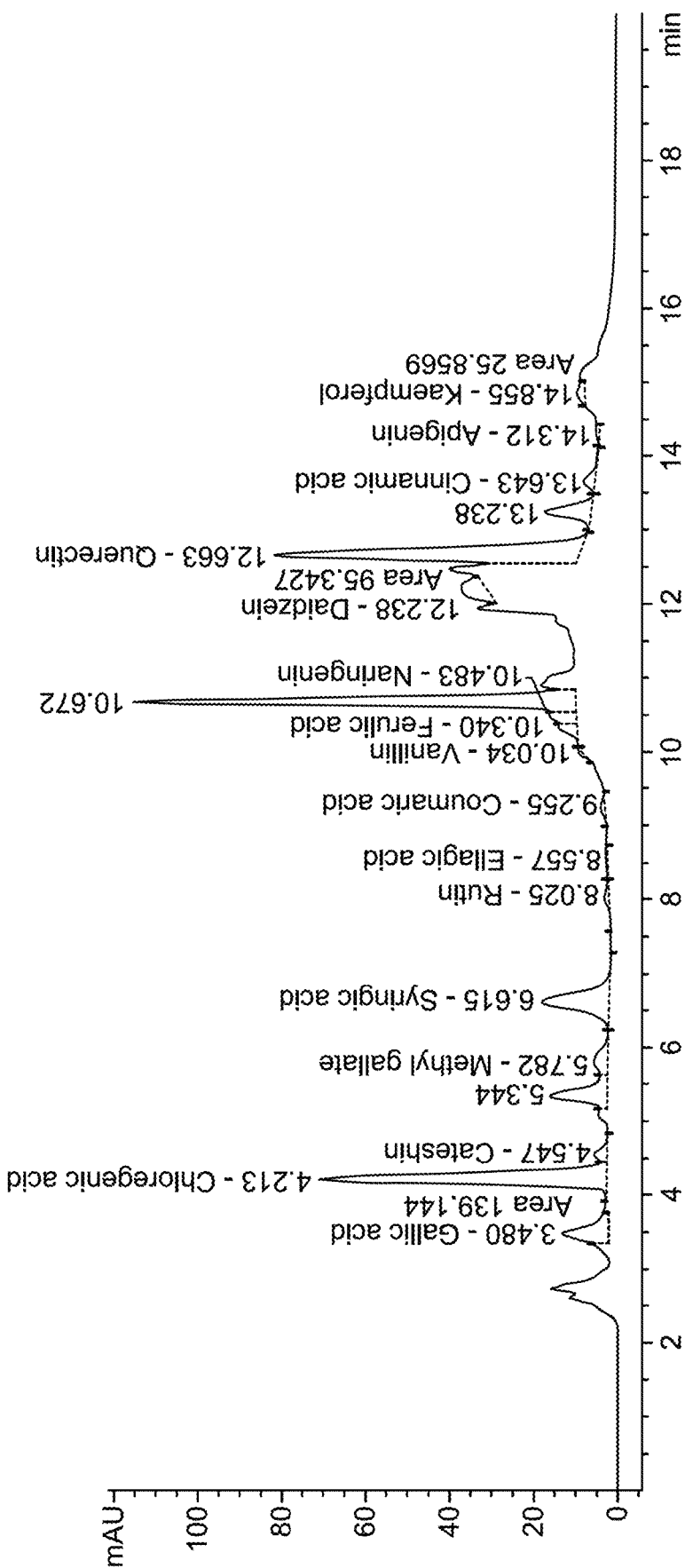
FIG. 3A shows a high-performance liquid chromatogram (HPLC) of phenolic compounds in OPE, according to certain embodiments.
Figure 3B:
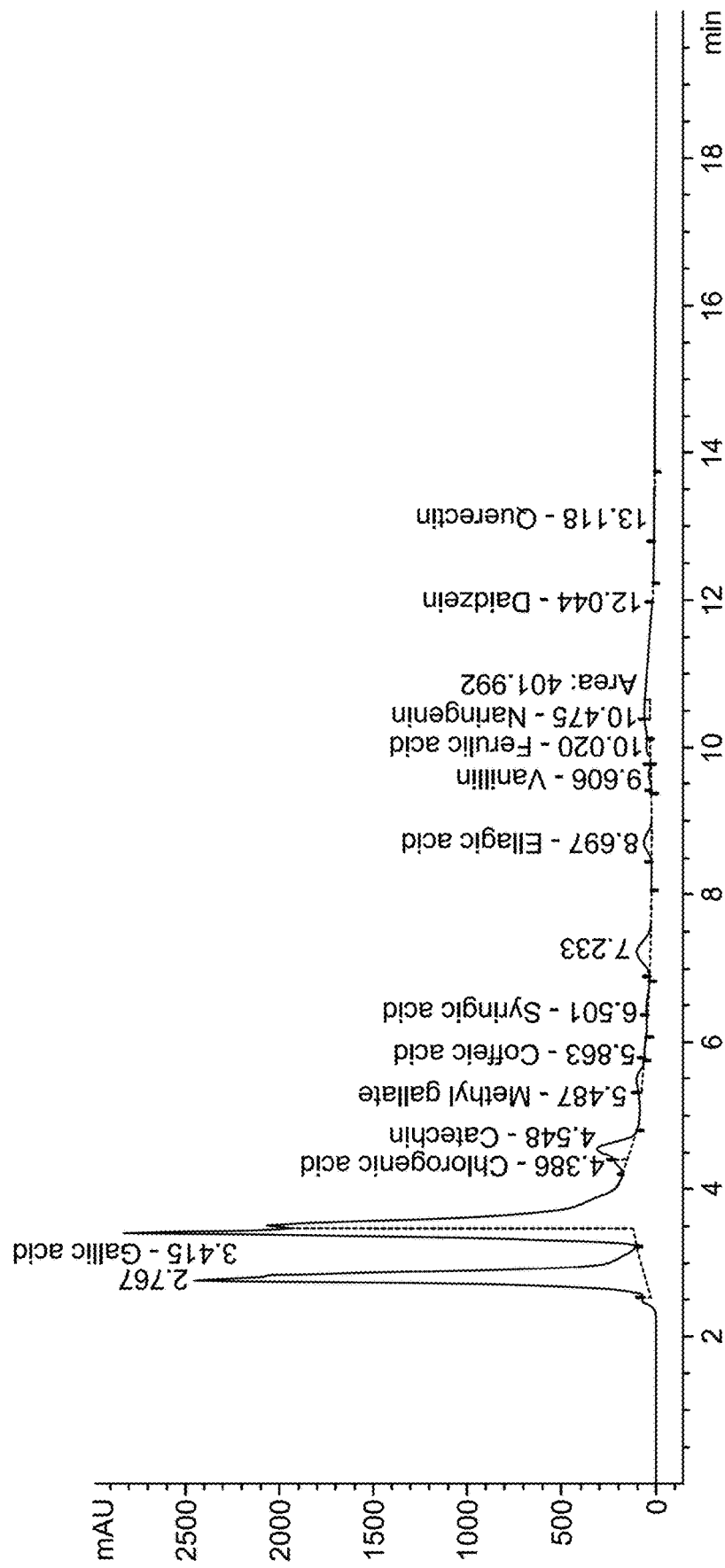
FIG. 3B shows an HPLC of phenolic compounds in PPE, according to certain embodiments.
Figure 4:
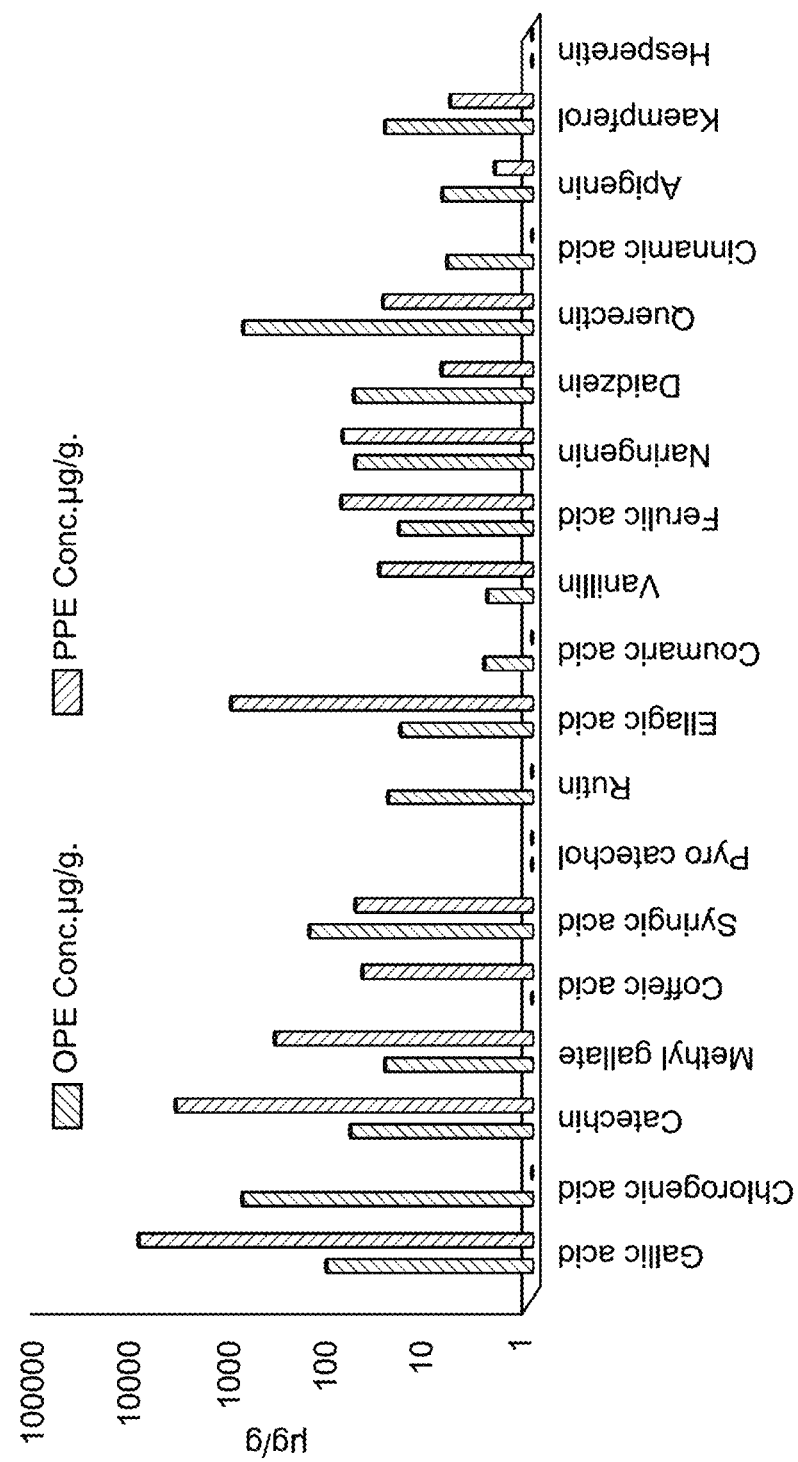
FIG. 4 shows an HPLC analysis of phenolic compounds in OPE and PPE, according to certain embodiments.

Example 5: Identification of Phenolic Compounds in OPE and PPE by High-Performance Liquid Chromatography (HPLC) Analysis Plant extracts with phenolic compounds, like OPE and PPE, exhibit anti-bacterial, anti-inflammatory, and antioxidant properties, as identified through HPLC analysis and High-performance liquid chromatography with diode-array detection (HPLC-DAD) (FIG. 3A and FIG. 3B). Table 3, FIG. 3A, FIG. 3B & FIG. 4 illustrate the diverse array of flavonoids and phenolics identified in PPE and OPE extracts via HPLC analysis, with PPE exhibiting higher levels of gallic acid, catechin, and elagic acid, while OPE contained elevated levels of chlorogenic acid, syringic acid, and quercetin. The data presented in Table 3, FIG. 3A, FIG. 3B and FIG. 4 showed high levels of gallic acid, catechin, and elagic acid, with concentrations of 10050.45, 4490.18, and 1161.19 µg/g, respectively, for PPE. In contrast, OPE contained elevated chlorogenic acid, syringic acid, and quercetin levels, ranging from 1003.28 to 937.94 µg/g. While PPE had minimal quercetin content, OPE showed a significant presence. Conversely, OPE had lower levels of ellagic and gallic acid than PPE. Additionally, OPE lacked coffee acid, present in PPE at 54.91 µg/g. Coumaric acid and rutin were absent in PPE but present in OPE at 28.63 and 3.13 µg/g, respectively. Notably, OPE exhibited higher chlorogenic acid, kaempferol, daidzein, and naringenin levels than PPE. Conversely, vanillin and ferulic acid levels were increased in PPE as compared to in OPE, with concentrations of 37.58 and 92.03 µg/g, respectively, compared to 2.92 and 23.27 µg/g.

TABLE 1

HPLC analysis of phenolic compound concentrations in OPE and PPE.

| Phenolic Compounds | OPE | | PPE | |
| --- | --- | --- | --- | --- |
| | µg/ml | µg/g | µg/ml | µg/g |
| Gallic acid | 12.36 | 123.55 | 502.52 | 10050.45 |
| Chlorogenic acid | 100.33 | 1003.28 | 0.00 | 0.00 |
| Catechin | 7.43 | 74.26 | 224.51 | 4490.18 |
| Methyl gallate | 3.18 | 31.81 | 21.84 | 436.87 |
| Coffeic acid | 0.00 | 0.00 | 2.75 | 54.91 |
| Syringic acid | 19.33 | 193.33 | 3.16 | 63.27 |
| Pyro catechol | 0.00 | 0.00 | 0.00 | 0.00 |
| Rutin | 2.86 | 28.63 | 0.00 | 0.00 |
| Ellagic acid | 2.18 | 21.84 | 58.06 | 1161.19 |
| Coumaric acid | 0.31 | 3.13 | 0.00 | 0.00 |
| Vanillin | 0.29 | 2.92 | 1.88 | 37.58 |
| Ferulic acid | 2.33 | 23.27 | 4.60 | 92.03 |
| Naringenin | 6.26 | 62.60 | 4.44 | 88.86 |
| Daidzein | 6.55 | 65.50 | 0.40 | 7.93 |
| Quercetin | 93.79 | 937.94 | 1.76 | 35.23 |

TABLE 1-continued

HPLC analysis of phenolic compound
concentrations in OPE and PPE.

| Phenolic Compounds | OPE | | PPE | |
|---|---|---|---|---|
| | µg/ml | µg/g | µg/ml | µg/g |
| Cinnamic acid | 0.73 | 7.34 | 0.05 | 0.99 |
| Apigenin | 0.80 | 7.96 | 0.12 | 2.44 |
| Kaempferol | 3.20 | 32.03 | 0.34 | 6.87 |
| Hesperetin | 0.00 | 0.00 | 0.00 | 0.00 |

Example 6: Characterizations by SEM and FT-IR of Chitosan Seed Nanoparticles (CSNP), Onion Peel Extract Encapsulated in Chitosan Seed Nanoparticles (OPE-CSNP), and Pomegranate Peel Extract Encapsulated in Chitosan Seed Nanoparticles (PPE-CSNP)

Figure 5:
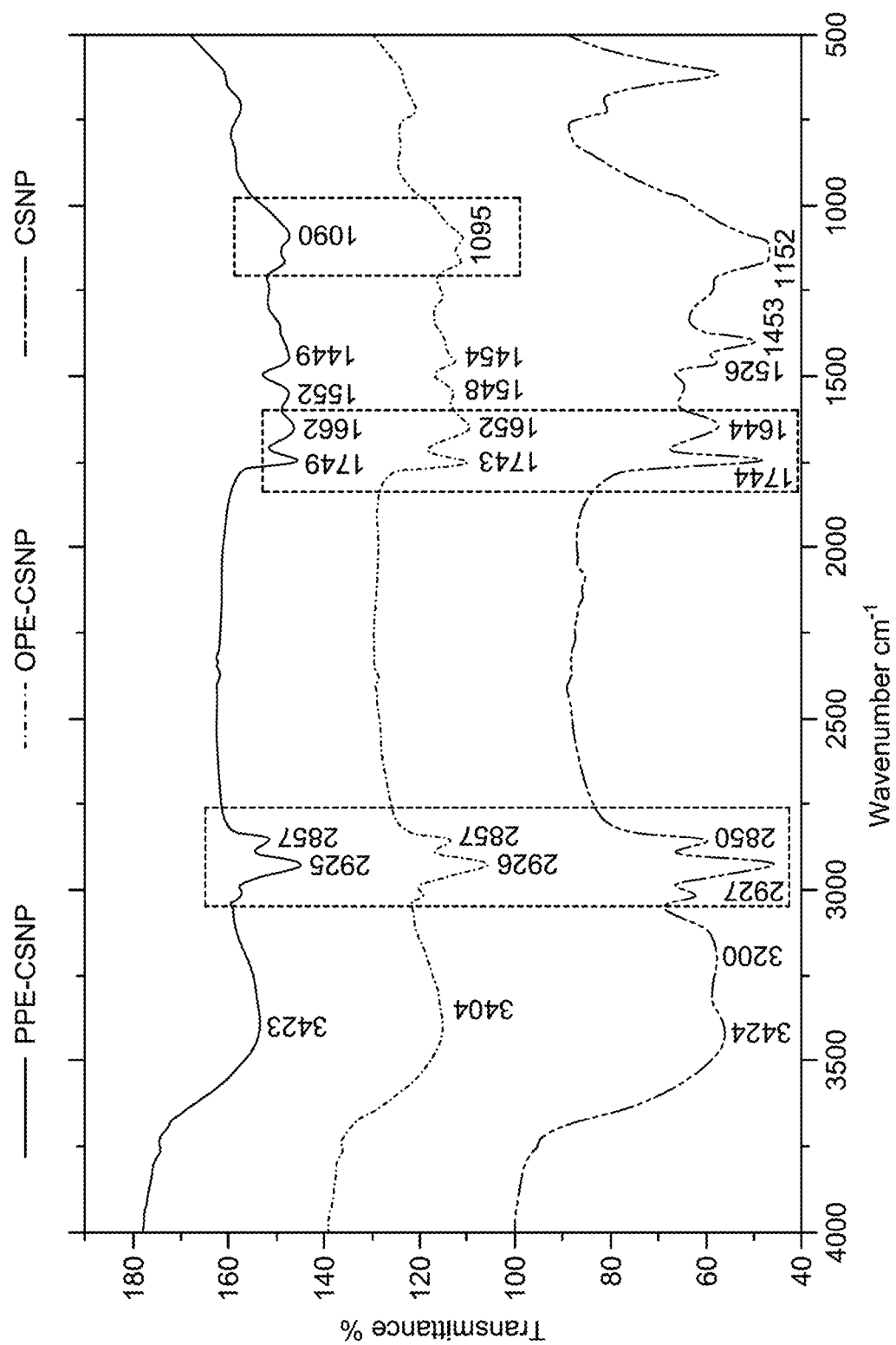
FIG. 5 shows a Fourier transform infrared spectroscopy (FT-IR analysis) of nanoparticle chia seeds (CSNP), PPE-CSNP, and OPE-CSNP, according to certain embodiments.

FT-IR analysis was done to understand the encapsulation of bioactive compounds from PPE and OPE within chia seed nanoparticles. FIG. 5 shows the FTIR spectra of CSNP, CSNP encapsulated with bioactive pomegranate peel extract PPE-CSNP, and CSNP encapsulated with bioactive onion peel extract OPE-CSNP. In the chia FTIR spectrum, FIG. 5, a broad peak at 3200 cm$^{-1}$ indicates the presence of the O—H group, while a peak at 1152 cm$^{-1}$ corresponds to the vibration of (C—O—C) in the carbohydrate backbone. The broad peak at 3424 and bands at 1453 and 1526 cm$^{-1}$ can be attributed to the symmetric stretching of the carboxylate group (—COO—) found in chia seed acids. Additionally, the peaks at 3424 cm$^{-1}$ and 1526 cm$^{-1}$ correspond to the O—H stretch and phenyl rings of polyphenolic compounds, respectively. The asymmetric and symmetric vibrations of —C—H at 2927 cm$^{-1}$ to 2857 cm$^{-1}$ indicate tocopherol. Peaks at 1744 cm$^{-1}$, 1644 cm$^{-1}$, and 1400 cm$^{-1}$ represent vibrations of (CO) ester from terpene alkaloids, (C=O) quinoid ring, and (CH2) methylene group, respectively. FTIR analysis was further utilized to determine if the encapsulation of bioactive compounds from PP and OP within chia seed nanoparticles involved chemical or physical entrapment. No or minimal changes in the FTIR spectrum compared to the parental compounds indicated physical entrapment, while spectral shifts suggested possible chemical interactions between PPE or OPE and chia seed nanoparticles (CSNP). Comparing the FTIR spectra of CSNP, PPE-loaded CSNP, and OPE-loaded CSNP revealed no spectral changes, confirming the physical entrapment of PPE and OPE within CSNP (FIG. 5). Furthermore, the addition of PPE to CSNP resulted in significant changes in the intensity of C—H stretching bands at various wavenumbers (3785 cm$^{-1}$, 2925 cm$^{-1}$, 2857 cm$^{-1}$, 1552 cm$^{-1}$, 1449 cm$^{-1}$, and 1090 cm$^{-1}$), and the addition of OPE to CSNP resulted in significant changes in the intensity of C—H stretching bands at different wavenumbers (3760 cm$^{-1}$, 3404 cm$^{-1}$, 2926 cm$^{-1}$, 2857 cm$^{-1}$, 1743 cm$^{-1}$, 1548 cm$^{-1}$, 1454 cm$^{-1}$, and 1095 cm$^{-1}$). These changes indicated the successful incorporation of both PP and OP into CN.

Figure 6A:
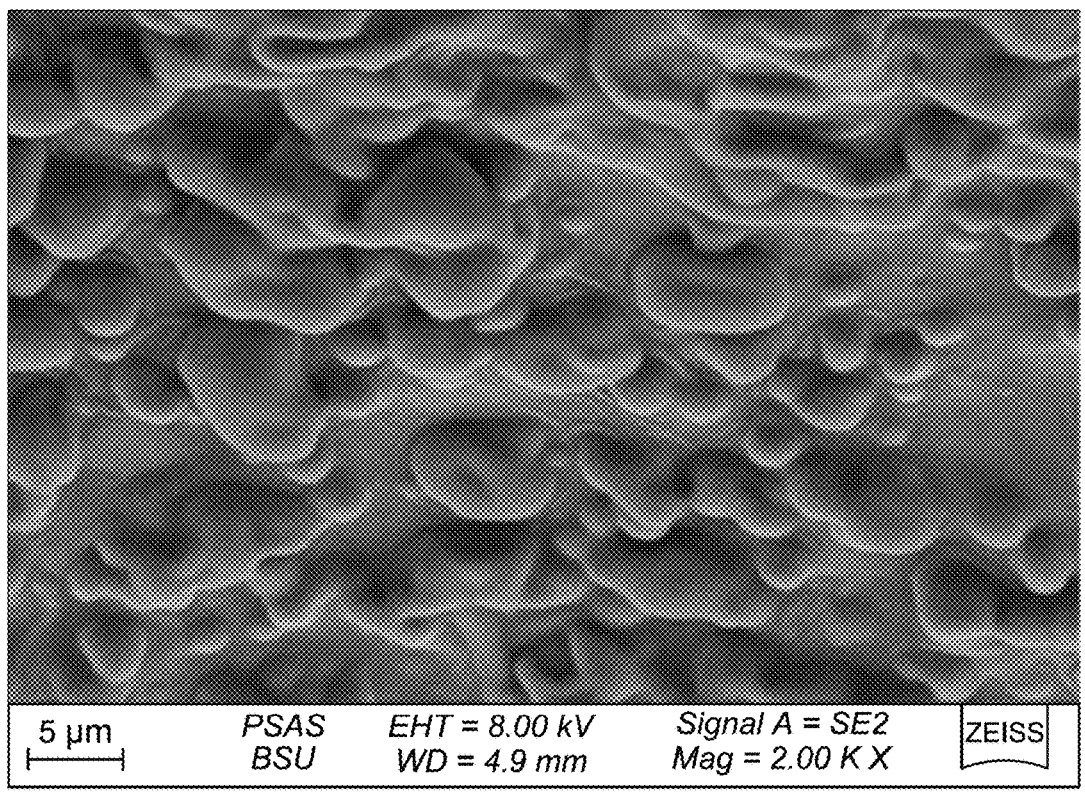
FIG. 6A and FIG. 6B show scanning electron micrographs (SEM) of PPE-CSNP, according to certain embodiments.
Figure 6B:
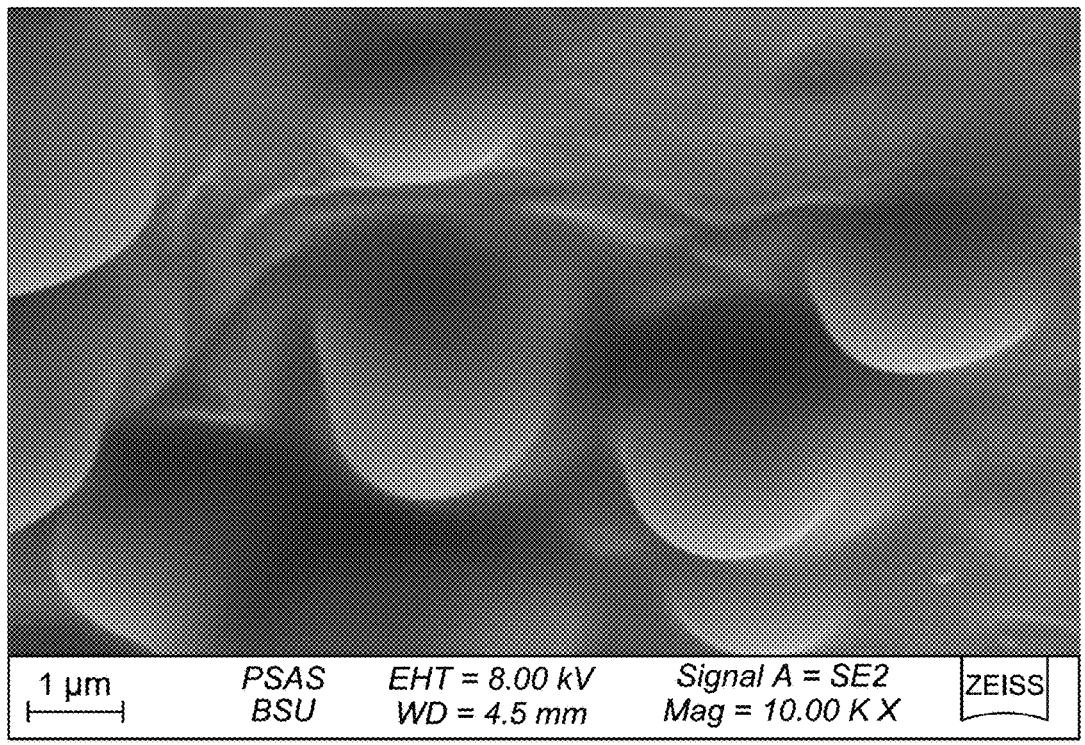
Figure 6C:
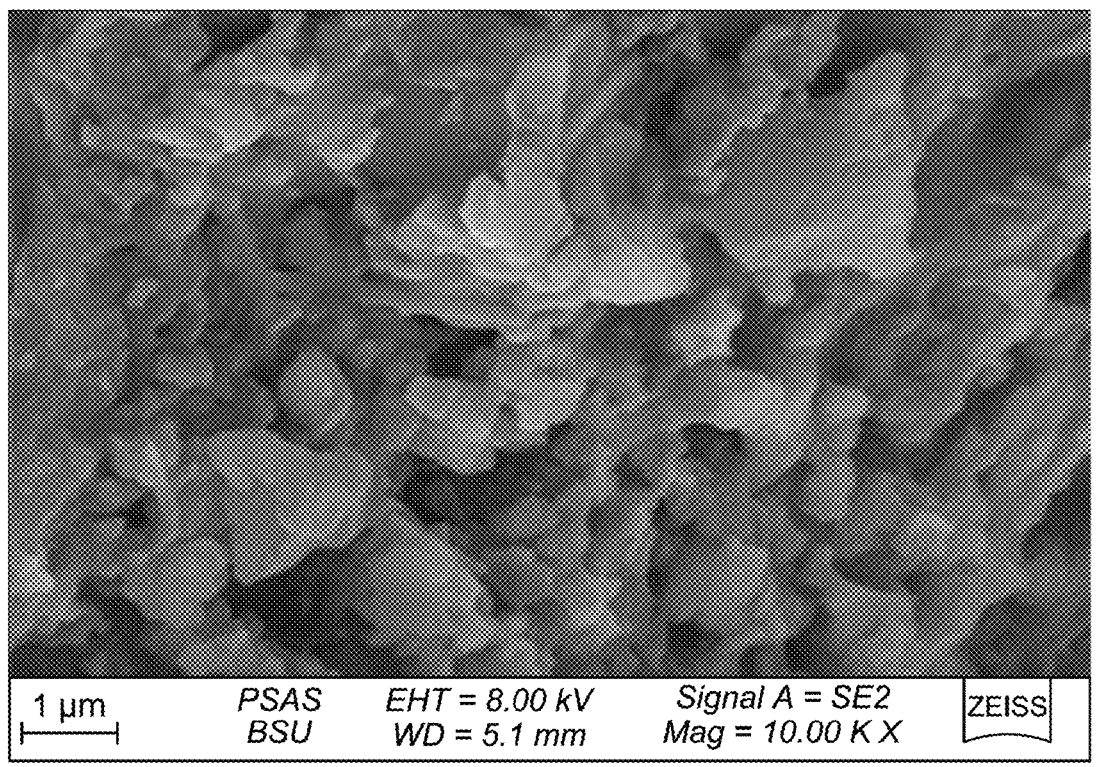
FIG. 6C and FIG. 6D show SEMs of OPE-CSNP, according to certain embodiments.
Figure 6D:
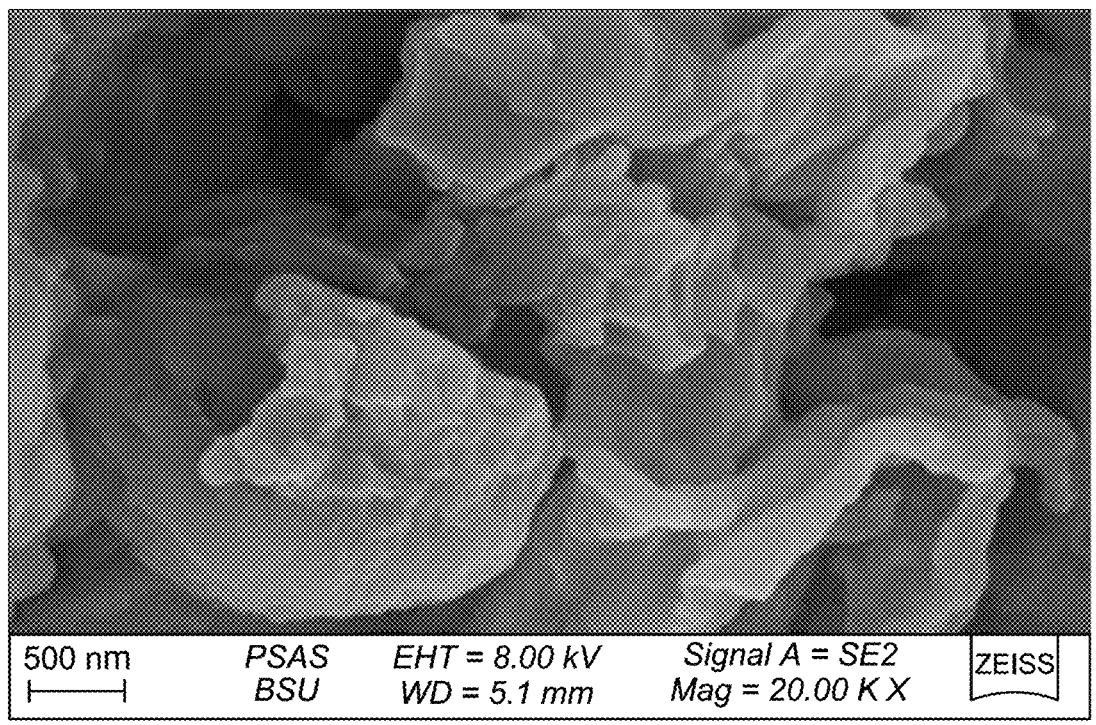

SEM images depict the surface morphology of chia-modified pomegranate (FIG. 6A & FIG. 6B) and onion peels (FIG. 6C & FIG. 6D), respectively, confirming successful modification compared to raw chia seeds, which had an elliptical, smooth, and glabrous surface. The SEM images reveal differences in surface morphology among the samples, with chia-modified pomegranate exhibiting protrusions and chia-modified onion peels displaying a rough surface with numerous pores.

Example 7: Zeta Potential of PPE-CSNP and OPE-CSNP

The zeta potential, indicating the stability of synthesized nanoparticles, was measured for OPE-CSNP and PPE-CSNP, yielding values of −22.1 and −20.3 mV, respectively, signifying successful chia seed modification by OPE and PPE. The negative values of Zeta potential are attributed to the presence of phenolic groups in chia seeds, known for their negative zeta potential values due to polyphenolic compounds, thus affirming the high activity of these new materials against gram-positive bacteria.

Example 8: Thermal Gravimetric Analysis (TGA) and Differential Thermal Analysis (DTA) (Thermal Analysis) of PPE-CSNP and OPE-CSNP TGA and DTG analyses of CSNP encapsulated with bioactive pomegranate peels (PPE-CSNP) and onion peels (OPE-CSNP) revealed three primary phases of weight loss, with initial dehydration occurring around 25-122° C. for OPE-CSNP and 25-139° C. for PPE-CSNP. Both samples showed comparable water absorption capabilities. The derivative thermogravimetry (DTG) plots indicated a significant weight loss peak around 350° C., attributed to protein and carbohydrate degradation, with OPE-CSNP and PPE-CSNP exhibiting temperature ranges of approximately 198-459° C. and 200-502° C., respectively. At 850° C., residual masses were 5.60% for OPE-CSNP and 30.30% for PPE-CSNP under an inert atmosphere, with PPE-CSNP displaying higher thermal stability up to 500° C. but lower stability between 500-850° C. possibly due to oil presence.

Example 9: X-Ray Diffraction Characteristics (XRD) of PPE-CSNP and OPE-CSNP

Figure 7:
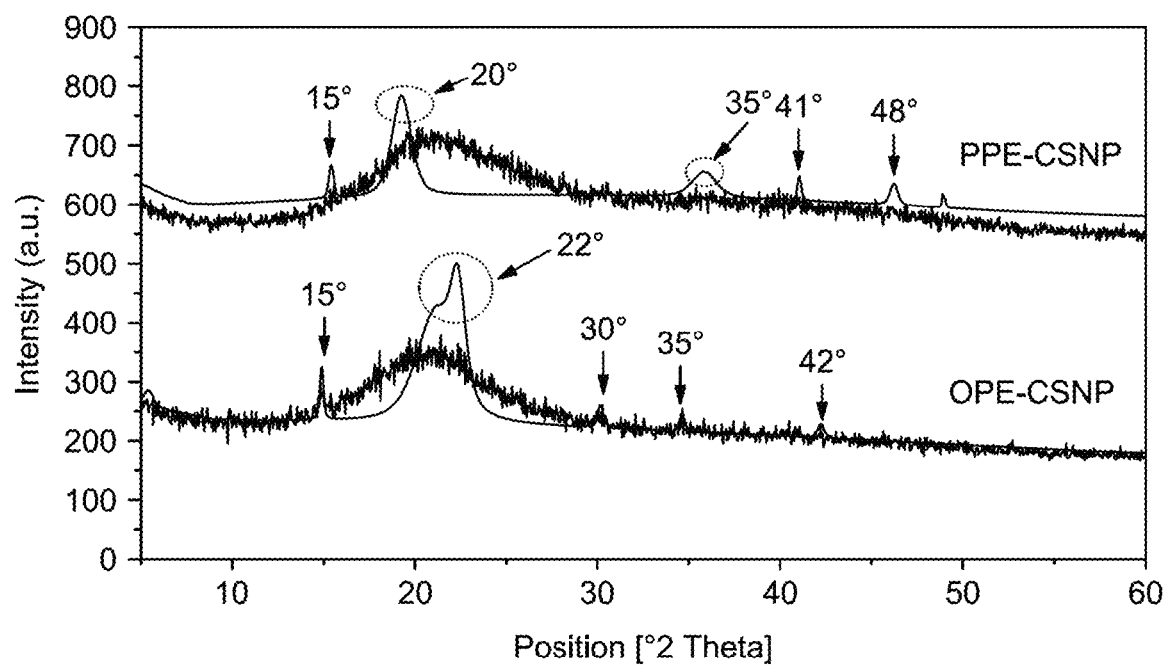
FIG. 7 shows X-ray diffraction characteristics (XRD) of PPE-CSNP and OPE-CSNP, according to certain embodiments.

FIG. 7 depicts the XRD patterns of PPE-CSNP and OPE-CSNP. The PPE-CSNP exhibited distinct peaks, including two broad peaks at approximately 20° and 35° (2θ) and three sharp peaks at 15°, 41°, and 48° (2θ). On the other hand, OPE-CSNP displayed a broad peak at around 22° (2θ) and four smaller, sharp peaks at approximately 15°, 30°, 35°, and 42° (2θ). The crystallite size of PPE-CSNP was 72.20 Å, while OPE-CSNP's was 36.17 Å, indicating distinct crystalline structures for both. Surface morphologies were consistent with these results. PPE-CSNP exhibited a higher basal spacing (4.6 Å) than OPE-CSNP (4.2 Å), suggesting more layers and pores.

Example 10: Antibacterial Activity of OPE and PPE Well Diffusion OPE-CSNP and PPE-CCSNP Assay The investigation focused on the antibacterial properties of extracts derived from onion peel, pomegranate peel, and chia seed, particularly when encapsulated in nanoformulations (OPE-CSNP and PPE-CSNP). The extracts, known for their richness in bioactive compounds like phenolic compounds, flavonoids, and tannins, were explored for potential health benefits against various microbes. The study employed the inhibition zone diameter to evaluate the effectiveness of these natural extracts in inhibiting microbial growth, thereby assessing their antimicrobial properties.

Figure 8:
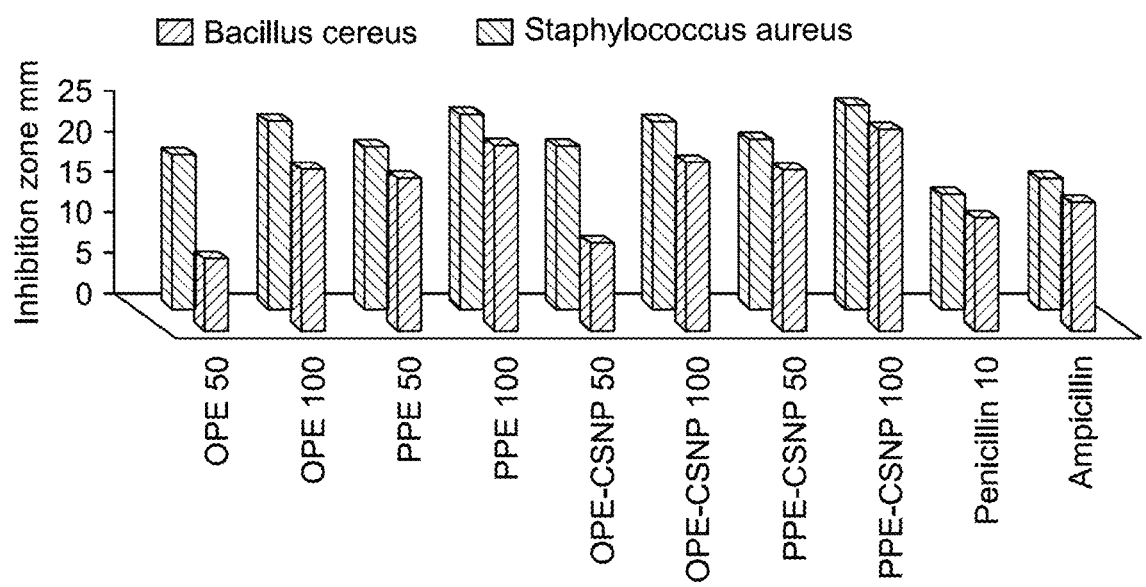
FIG. 8 shows the antibacterial activity of OPE, PPE OPE-CSNP, and PPE-CSNP at various concentrations against *Bacillus cereus* and *Staphylococcus aureus* by well diffusion method, according to certain embodiments.
Figure 9B:
FIG. 9B shows the antibacterial activity of PPE against *S. aureus*, according to certain embodiments.
Figure 9D:
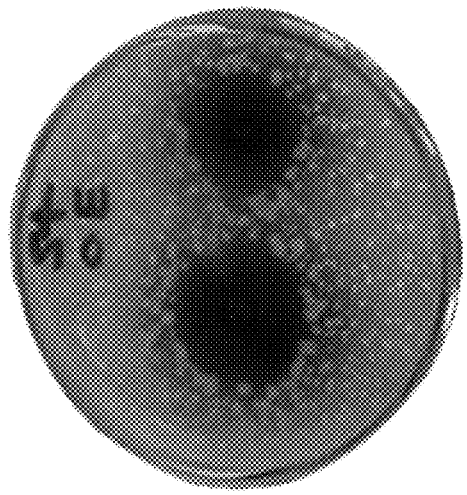
FIG. 9D shows the antibacterial activity of OPE against *S. aureus*, according to certain embodiments.
Figure 9A:
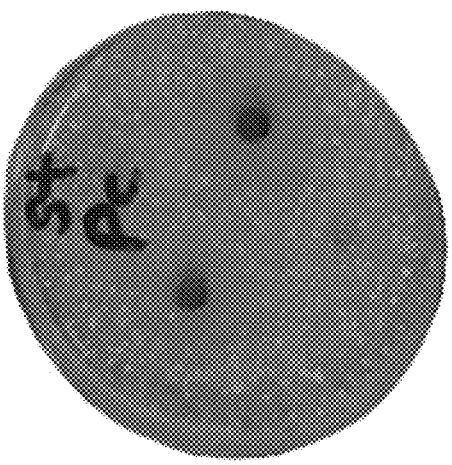
FIG. 9A shows the antibacterial activity of PPE-CSNP against *S. aureus*, according to certain embodiments.
Figure 9C:
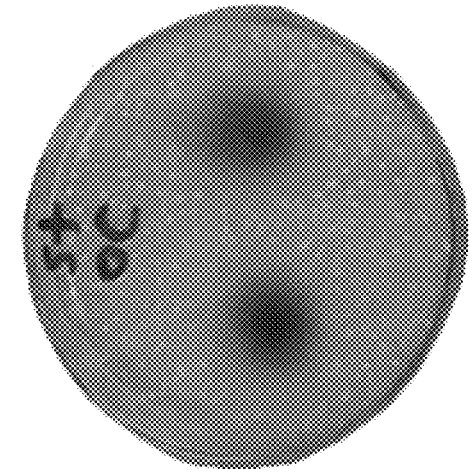
FIG. 9C shows the antibacterial activity of OPE-CSNP (C) against *S. aureus*, according to certain embodiments.
Figure 10B:
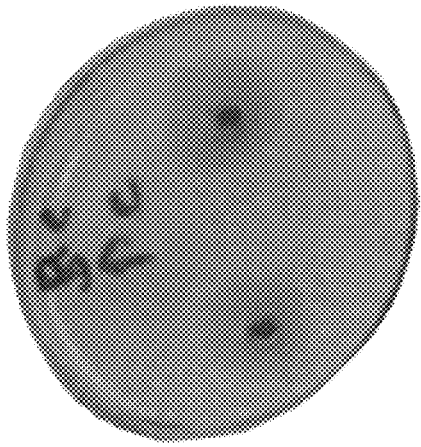
FIG. 10B shows the antibacterial activity of PPE-CSNP against *B. cereus*, according to certain embodiments.
Figure 10D:
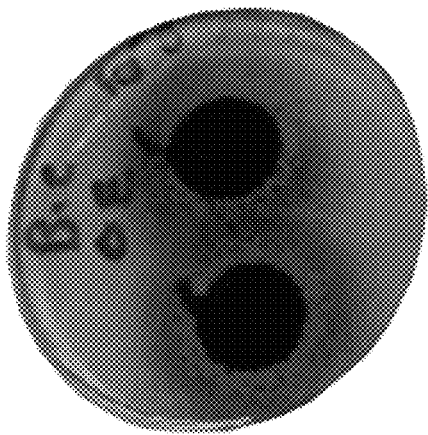
FIG. 10D shows the antibacterial activity of OPE against *B. cereus*, according to certain embodiments.
Figure 10A:
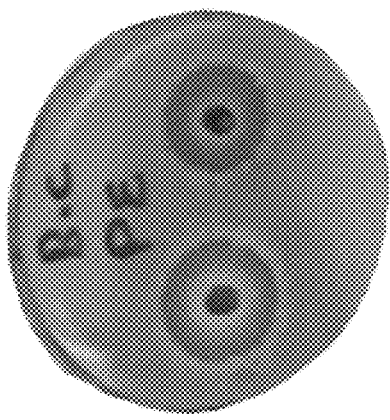
FIG. 10A shows the antibacterial activity of PPE against *B. cereus*, according to certain embodiments.
Figure 10C:
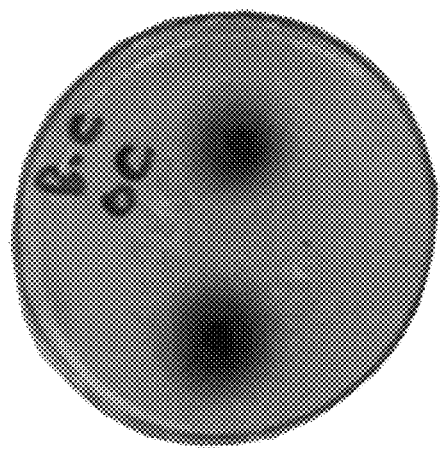
FIG. 10C shows the antibacterial activity of OPE-CSNP against *B. cereus*, according to certain embodiments.

According to the findings in Table 4, FIG. 8 to FIG. 10, PPE-CSNP at 100 µl/well displayed the largest zone of inhibition, measuring 25 mm against both *S. aureus* and *B. cereus*. In comparison, OPE at 100 µl/well showed the smallest zones of inhibition at 23 mm and 20 mm for *S. aureus* and *B. cereus*, respectively. Further analysis revealed that PPE-CSNP at 100 µl/well exhibited the highest zone of inhibition against *S. aureus*, while OPE at 50 µl/well demonstrated the lowest. Conversely, PPE-CSNP at 100 µl/well showed the highest zone of inhibition against *B. cereus*, whereas OPE at 50 µl/well displayed the lowest. Comparisons with conventional antibiotics, such as penicillin and ampicillin, indicated that the antibacterial effects of the extracts were comparable or even superior. These results suggest that nano-encapsulated extracts, particularly those loaded with CSNP from OP and PP, could be effective alternatives to conventional antibiotics. Moreover, these composites show promise as food preservatives, potentially extending shelf life, given their moderate antimicrobial activity against *B. cereus* and *S. aureus*.

The specific antibacterial efficacy of OPE was attributed to its rich content of strong antibacterial chemicals like quercetin and kaempferol. The extract demonstrated significant inhibition of various bacterial strains, particularly *S. aureus* and *E. coli*, as reported in the literature. The proposed mechanism of action involves damage to bacterial cell membranes and inhibiting vital enzymes associated with bacterial metabolism. Similarly, PPE, abundant in polyphenolic compounds like ellagic acid and punicalagin, exhibited notable antibacterial properties. The extract displayed significant inhibitory effects against pathogenic bacteria, including *S. typhimurium* and *B. cereus*. The suggested mechanism involves disrupting bacterial cell membranes and interfering with microbial adhesion and biofilm formation.

TABLE 4

Antibacterial activity of OPE, PPE, OPE-CSNPs, and PPE-CSNPs well diffusion assay (inhibition zone diameter in mm).

| Sample | Concentration (µl/well) | Inhibition zone diameter (mm) | |
|---|---|---|---|
| | | S. aureus | B. cereus |
| OPE | 50 | 19 | 9 |
| | 100 | 23 | 20 |
| PPE | 50 | 20 | 19 |
| | 100 | 24 | 23 |
| OPE-CSNPs | 50 | 20 | 11 |
| | 100 | 23 | 21 |
| PPE-CSNPs | 50 | 21 | 20 |
| | 100 | 25 | 25 |
| Penicillin | 10 µl | 14 | 14 |
| Ampicillin | 10 µl | 16 | 16 |

Example 11: Antifungal and Yeast Activity of OPE and PPE and OPE-CCSNP and PPE-CSNP by Well Diffusion Assay (Inhibition Zone Diameter Mm)

Figure 11:
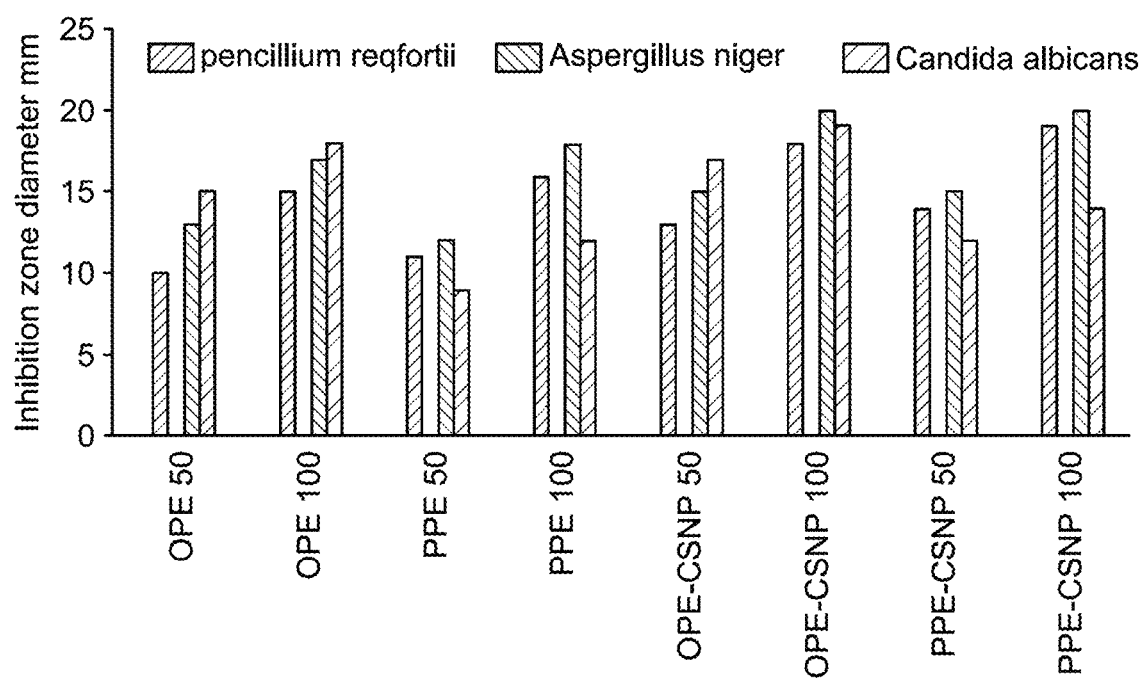
FIG. 11 is a graph showing the antifungal and yeast activity of OPE, PPE, OPE-CSNP, and PPE-CSNP, against *Pencillium reqfortii*, *Aspergillus niger*, and *Candida albicans*, according to certain embodiments.

The antifungal and yeast activities of OPE, PPE, OPE-CCSNP, and PPE-CSNP were evaluated by the well diffusion assay, focusing on the inhibition zone diameter measured in millimeters, as in Table 5 and (FIG. 11). In the qualitative assessment of antifungal activity against *C. albicans*, *A. niger*, and *P. reqfortii*, all extracts exhibited strong inhibitory effects, as indicated by the measured inhibition zone diameters. Notably, OPE-CSNP demonstrated heightened efficacy against all tested strains at a concentration of 100 µl. The inhibition zone diameters were 19, 20, and 18 mm for *C. albicans*, *A. niger*, and *P. reqfortii*, respectively.

PPE-CSNP followed in effectiveness, with notable sensitivity observed in *A. niger* and *P. reqfortii*, showing inhibition zone diameters of 20 and 19 mm, respectively. However, *C. albicans* exhibited higher resistance to PPE-CSNP and PPE at a concentration of 100 µl, with inhibition zone diameters of 14 and 12 mm, respectively.

These findings align with previous studies in the literature supporting the observed results. The comparative analysis indicates that OPE-CSNP and PPE-CSNP are potent against various fungi, with potential applications in addressing fungal infections. The variation in sensitivity among the tested strains suggests the importance of considering the specific fungal species when assessing the antifungal properties of these extracts.

The results highlight the potential of OPE-CSNP and PPE-CSNP as promising antifungal agents, showcasing their effectiveness against common pathogenic fungi. Further exploration and understanding of the underlying mechanisms contributing to the antifungal properties of these extracts could provide valuable insights for future applications in both medical and pharmaceutical fields.

TABLE 5

Antifungal and yeasts activity of OPE, PPE, OPE-CSNP, and PPE-CSNP using well diffusion assay (Inhibition zone diameter mm)

| Sample | Concentration (µL/well) | Inhibition zone diameter mm | | |
|---|---|---|---|---|
| | | C. albicans | A. Niger | P. reqfortii |
| OPE | 50 | 15 | 13 | 10 |
| | 100 | 18 | 17 | 15 |
| PPE | 50 | 9 | 12 | 11 |
| | 100 | 12 | 18 | 16 |
| OPE-CSNP | 50 | 17 | 15 | 13 |
| | 100 | 19 | 20 | 18 |
| PPE-SCNP | 50 | 12 | 15 | 14 |
| | 100 | 14 | 20 | 19 |

Example 12: Minimum Inhibitory Concentration (MIC) Values of OPE and PPE, OPE-CSNP, and PPE-CSNP Table 6 presents MIC values of OPE, PPE, OPE-CSNP, and PPE-CSNP against various microbes, revealing a range from 10 to 80 µg/mL based on the microorganism type. The MIC values for fungi were notably higher, ranging from 40 to 90 µg/mL. The enhanced antimicrobial activity observed in chia seed nanocomposites can be attributed to the synergistic effects between the bioactive compounds in the extracts and the chia seed matrix. The formulation of the nanocomposites likely facilitated a more controlled release and improved stability of the bioactive compounds, resulting in increased antimicrobial efficacy.

Example 13: Antibiofilm Potential

A tube-based assay evaluated the anti-biofilm activity of the synthesized OPE, PPE-CSNP, and PPE-CSNP against selected microbes. The study demonstrated the antibiofilm activity of OPE-CSNP, a potent chia seed extract, against *S. aureus*, a pathogenic bacterium known for its susceptibility to antimicrobial agents. The key findings include (i) uninhibited microbial growth and prominent ring formation in the absence of OPE-CSNP, contrasting with restricted growth in its presence; (ii) reduced biofilm formation by *S.*

Figure 12:
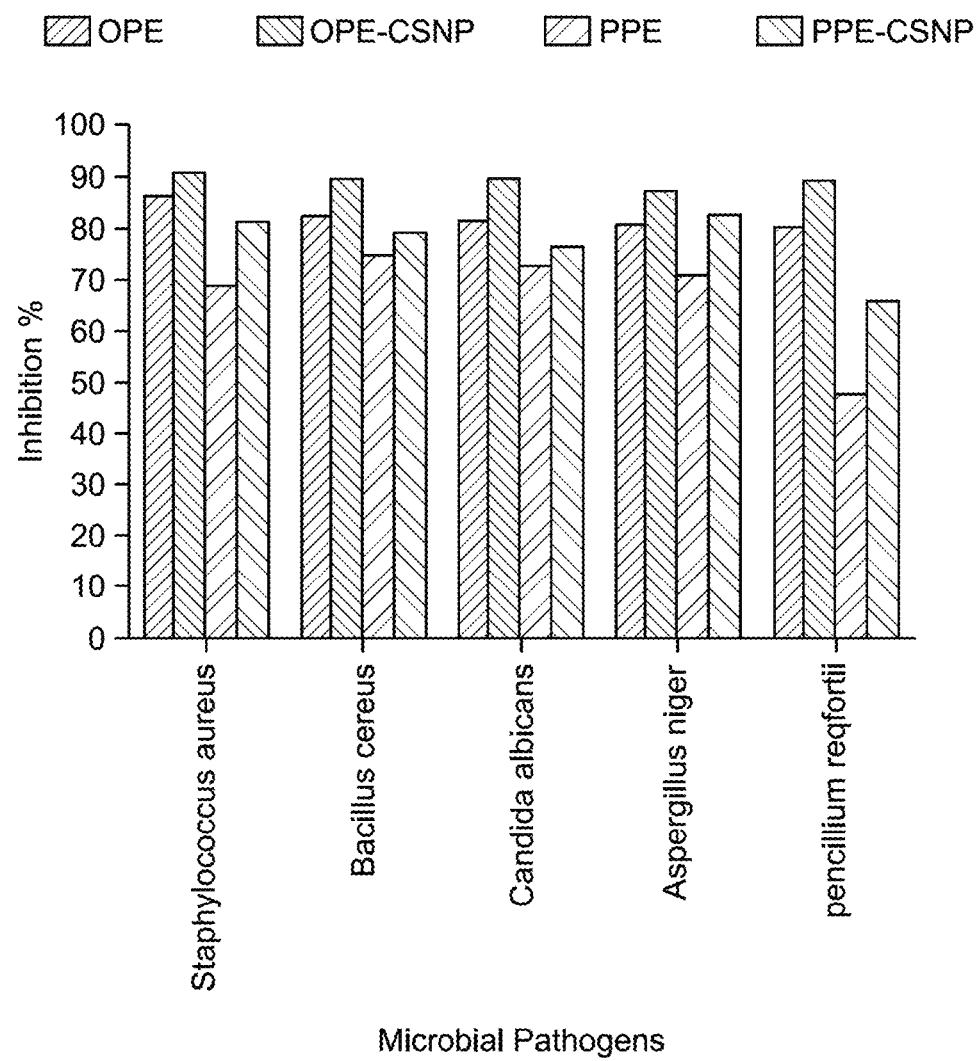
FIG. 12 shows antibiofilm activity of OPE, PPE, OPE-CSNP, and PPE-CSNP against different pathogenic bacteria and fungi, according to certain embodiments.

*aureus* upon treatment with OPE-CSNP, evident through less intense crystal violet staining; and (iii) a significantly higher percentage inhibition of *S. aureus* biofilm with OPE-CSNP compared to the control. The tube-based assay employed to assess antibiofilm activity revealed thick, whitish-yellow biofilm layers in control tubes, contrasting with the absence of biofilm layers and ring structures, pale adhered cell coloration, and minimal blue coloration upon ethanol addition in tubes treated with OPE-CSNP. The inhibition percentage was determined semi-quantitatively using a UV-visible spectrophotometer, correlating optical density at 570 nm with biofilm formation extent. FIG. 12 provides an overview of the antibiofilm activity of OPE, PPE-CSNP, and PPE-CSNP, shown as percentage inhibition, against various microbes.

Figure 14:
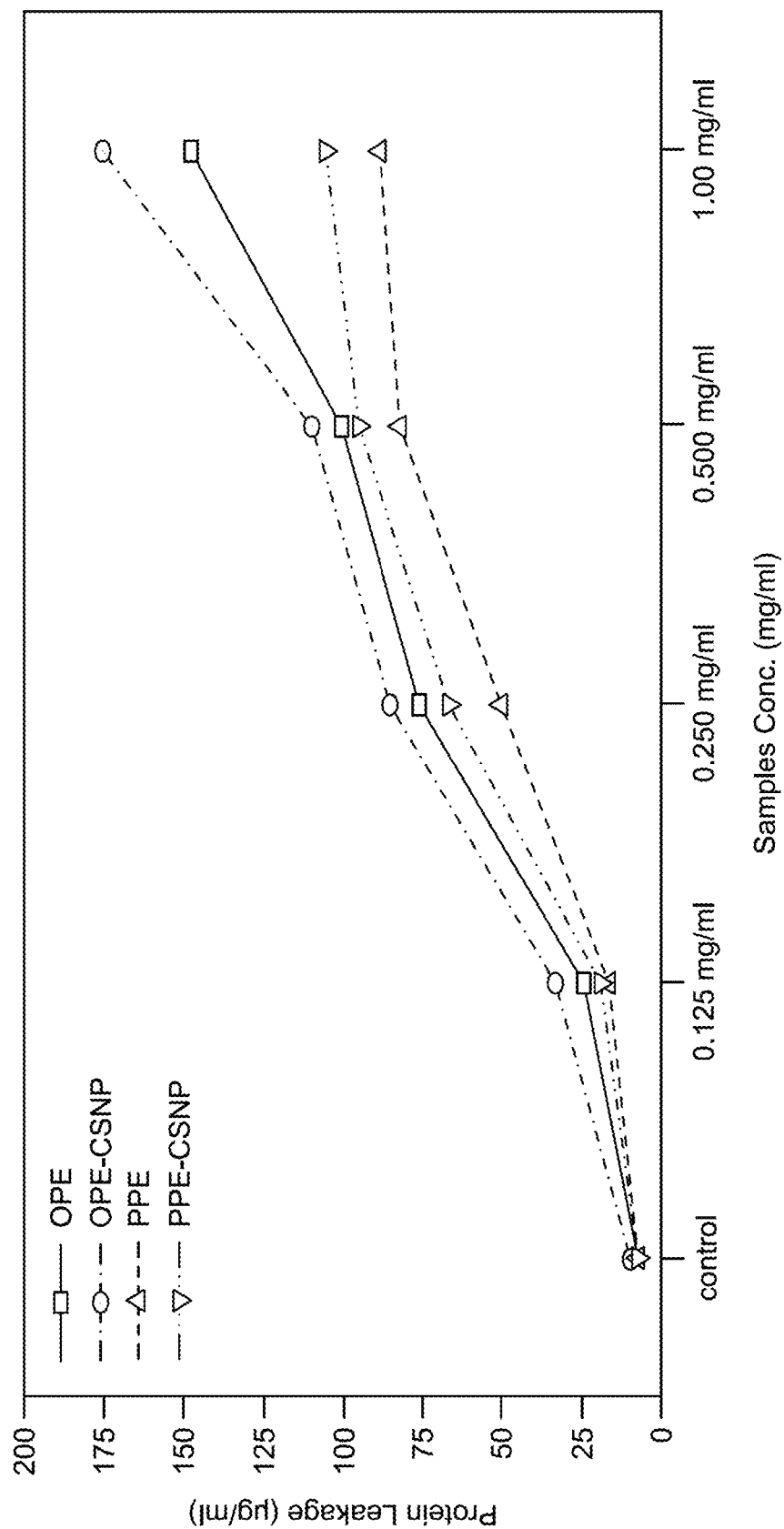
FIG. 14 shows the effect of OPE, PPE, OPE-CSNP, and PPE-CSNP on the protein leakage from *S. aureus* cell membranes, according to certain embodiments.

Table 6 shows the percentage inhibition after adding 10 μg/mL of OPE, PPE, OPE-CSNP, and PPE-CSNP. The highest inhibition was observed against *S. aureus* at 86.39%, followed by 82.32% for *B. cereus* and 81.18% for *C. albicans*. This demonstrates that biofilm formation is effectively controlled by inhibiting the initial adhesion phase, which is the first step in antimicrobial mechanisms.

highest antibacterial potency, significantly increasing membrane permeability compared to OPE, PPE, and PPE-CSNP, thus indicating membrane disruption as a key mechanism in inhibiting bacterial growth and suggesting the potential of OPE-CSNP for antibacterial applications (FIG. 14).

Figure 15:
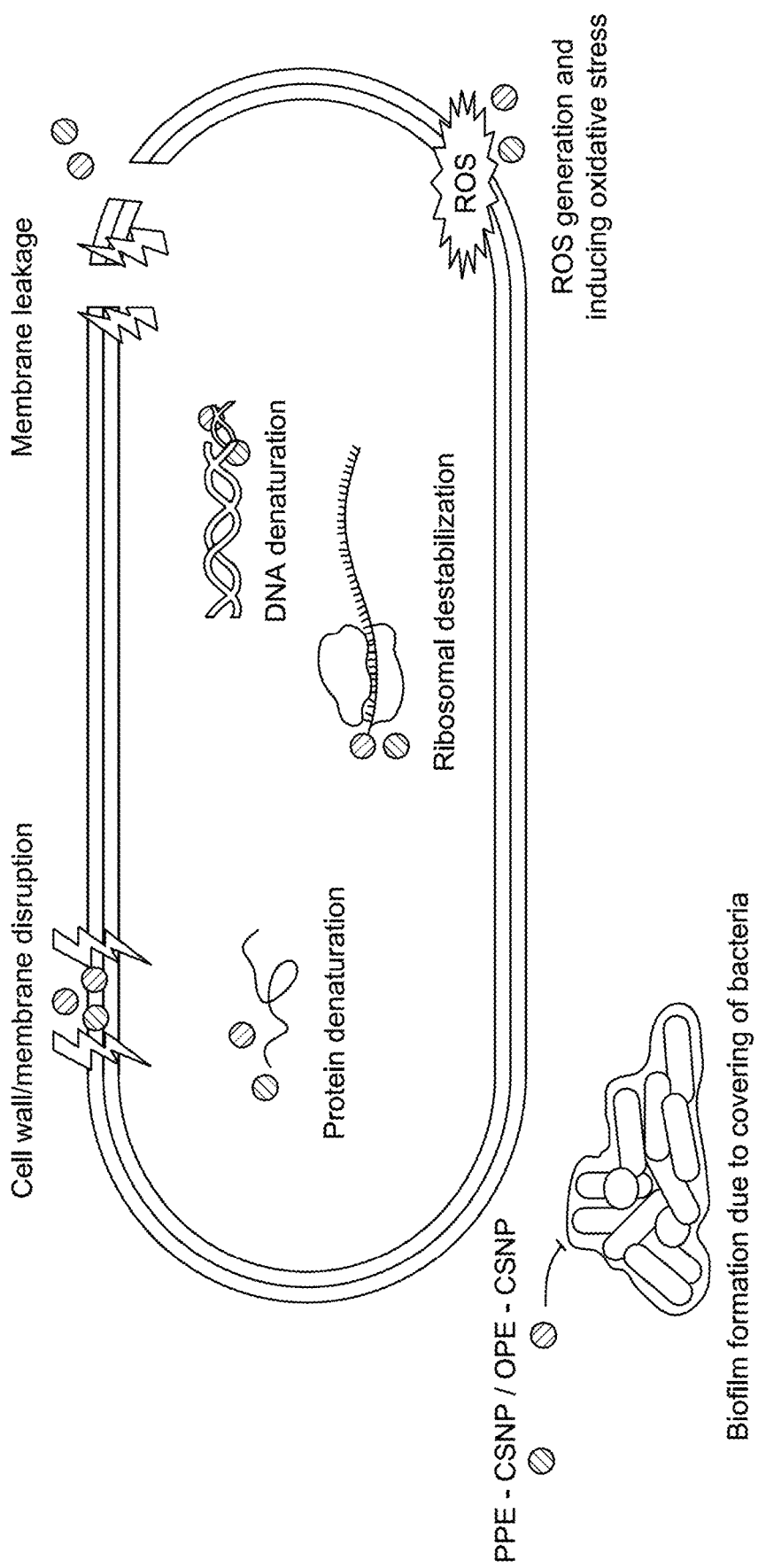
FIG. 15 is a schematic illustration depicting a mechanism of antibacterial activity of PPE-CSNP and OPE-CSNP, according to certain embodiments.

FIG. 15 illustrates the potential antimicrobial mechanisms, including the distribution of reactive oxygen species (ROS), particularly the superoxide anion, the action of nanoencapsulation (PPE-CSNP and OPE-CSNP) on bacterial cell walls, and an alkaline influence; metal nanoparticles are suggested to modify microbial morphology, inhibit biofilm formation, reduce microbial membrane permeability, and induce oxidative stress gene expression, primarily through hydrogen peroxide generation. The nanoencapsulation (PPE-CSNP and OPE-CSNP) initiates its function by adhering to the microbial cell's external surface, causing membrane damage, pit formation, and disruption of ion transport activity. Subsequently, nanoencapsulation particles distributed inside the microbial cell target intracellular structures such as plasmids, DNA, and other essential organelles. Ultimately, cellular toxicity ensues due to oxidative stress induced by ROS generation.

TABLE 6

Semiquantitative inhibition of biofilm formation by OPE, PPE, OPE-CSNPs, and PPE-CSNPs.

| | | O.D. of crystal violet stain at 570 nm | | | | Inhibition % | | | |
|---|---|---|---|---|---|---|---|---|---|
| Test organism | Control | Treated with OPE | Treated with PPE | Treated with OPE-CSNP | Treated with PPE-CSNP | OPE | PPE | OPE-CSNP | PPE-CSNP |
| *S. aureus* | $0.919^{ge} \pm 0.0065$ | $0.125^c \pm 0.0060$ | $0.288^c \pm 0.0043$ | $0.085^g \pm 0.0025$ | $0.175^c \pm 0.0051$ | 86.39 | 68.66 | 90.75 | 80.95 |
| *B. cereus* | $0.775^c \pm 0.070$ | $0.137^d \pm 0.0045$ | $0.198^d \pm 0.0054$ | $0.081^c \pm 0.0050$ | $0.161^h \pm 0.0042$ | 82.32 | 74.45 | 89.54 | 79.22 |
| *C. albicans* | $0.760^{de} \pm 0.0050$ | $0.143^e \pm 0.0046$ | $0.207^h \pm 0.0065$ | $0.079^{he} \pm 0.0045$ | $0.179^{he} \pm 0.0065$ | 81.18 | 72.76 | 89.60 | 76.44 |
| *A. niger* | $0.785^{hf} \pm 0.0020$ | $0.155^{ab} \pm 0.0036$ | $0.228^{ab} \pm 0.0042$ | $0.102^b \pm 0.0027$ | $0.136^{ab} \pm 0.005$ | 80.25 | 709.5 | 87.00 | 82.67 |
| *P. reqfortii* | $0.547 \pm 0.0025$ | $0.109^e \pm 0.0055$ | $0.287^e \pm 0.0046$ | $0.058^{fg} \pm 0.0036$ | $0.188^e \pm 0.0046$ | 80.07 | 47.53 | 89.39 | 65.63 |

The values are the means ± SDs (n = 3). The data within the groups were analyzed by one-way analysis of variance (ANOVA) followed by a, b, c, d, e, f, g, and h Duncan's multiple range test.

Figure 13:
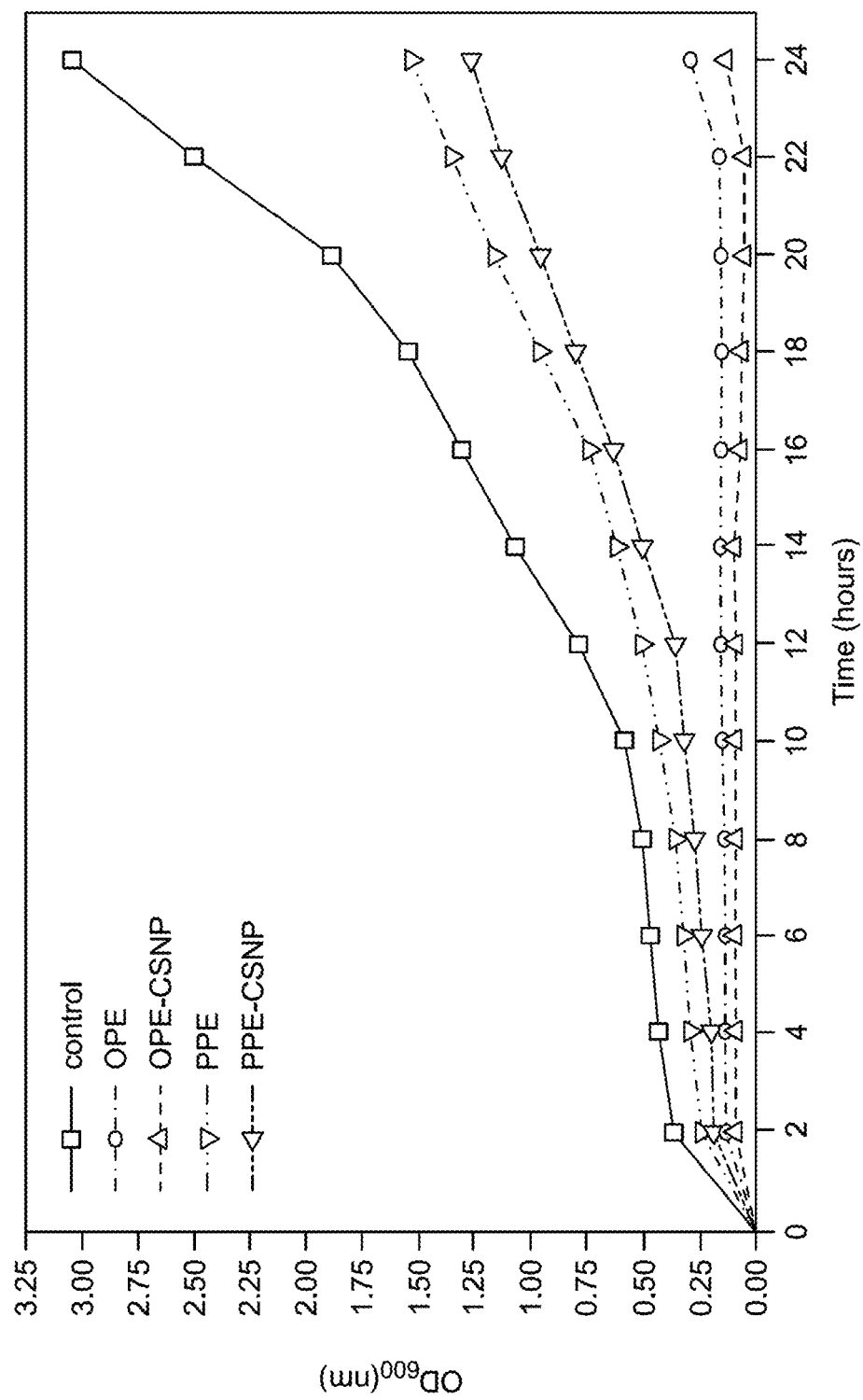
FIG. 13 shows the effect of OPE, PPE, OPE-CSNP, and PPE-CSNP on the growth curve of *S. aureus*, according to certain embodiments.

Example 14. Growth Curve Assay (Kinetic Study) of OPE, PPE, OPE-CSNP, and PPE-CSNP FIG. 13 demonstrates the inhibitory effect of OPE, PPE, OPE-CSNP, and PPE-CSNP on *S. aureus* growth, with optical density values significantly lower in their presence compared to the control sample, indicating growth inhibition. Among the samples, OPE-CSNP exhibited the most potent suppression of *S. aureus* growth, possibly due to the antimicrobial properties of onion extract and chia seed nanoparticles, as supported by previous studies. The synergy between chia seed's antibacterial effects and the bacteria-binding ability of OPE likely contributes to the observed maximum growth inhibition with OPE-CSNP, suggesting their potential as effective antibacterial agents.

Example 15. Determination of Protein Leakage from Bacterial Cell Membranes

The Bradford assay was employed to quantify protein release from *S. aureus* cells treated with OPE, PPE, OPE-CSNP, and PPE-CSNP, revealing concentration-dependent protein leakage, with treatments at 1.0 mg/mL resulting in protein releases of 147.35, 87.74, 175.21, and 105.29 μg/mL, respectively; notably, OPE-CSNP exhibited the Numerous modifications and variations of the present disclosure are possible in light of the above teachings. It is, therefore, to be understood that within the scope of the appended claims, the invention may be practiced otherwise than as specifically described herein.

The invention claimed is:

1. A food preservative having antimicrobial and antioxidant activity, comprising:
    an inner core comprising an extract of at least one of pomegranate peels and onion peels, and having a total phenols content of at least 167.09 mg GAE/g; and
    an outer coating comprising chia seed nanoparticles,
    wherein the food preservative is in the form of particles, and
    wherein the outer coating encapsulates the inner core.

2. The food preservative of claim 1, having a half maximal inhibitory concentration ($IC_{50}$) of 3.00 mg/mL or less against *Staphylococcus aureus* gram-positive bacteria.

3. The food preservative of claim 1, having an antimicrobial inhibition rate of 70% or greater against *Staphylococcus aureus* gram-positive bacteria.

4. The food preservative of claim 1, having an average particle size of 100 nm or less.

5. The food preservative of claim 1, having a surface with a plurality of protrusions.

6. The food preservative of claim 1, having a surface with a plurality of pores.

7. The food preservative of claim 6, wherein the plurality of pores have an average diameter of 35 nm or less.

8. The food preservative of claim 1, wherein at least one of the inner core and the outer coating comprises crystallites having a crystallite size of at least 35 Angstroms (Å).

9. The food preservative of claim 1, having a basal spacing of at least 4 Å.

* * * * *